(12) United States Patent
Begrow et al.

(10) Patent No.: US 10,889,066 B2
(45) Date of Patent: Jan. 12, 2021

(54) APPARATUS FOR FABRICATING AN ELASTIC NONWOVEN MATERIAL

(71) Applicant: Aurizon Ultrasonics, LLC, Kimberly, WI (US)

(72) Inventors: Brandon Leo Begrow, Hortonville, WI (US); Daniel James Sorensen, Neenah, WI (US); Thomas David Ehlert, Neenah, WI (US)

(73) Assignee: DUKANE IAS, LLC, St. Charles, IL (US)

( * ) Notice: Subject to any disclaimer, the term of this patent is extended or adjusted under 35 U.S.C. 154(b) by 0 days.

(21) Appl. No.: 15/718,872

(22) Filed: Sep. 28, 2017

(65) Prior Publication Data

US 2018/0093444 A1    Apr. 5, 2018

Related U.S. Application Data

(60) Provisional application No. 62/402,457, filed on Sep. 30, 2016.

(51) Int. Cl.
*B29C 65/00*    (2006.01)
*B29C 65/08*    (2006.01)
(Continued)

(52) U.S. Cl.
CPC .. *B29C 66/81435* (2013.01); *A61F 13/15739* (2013.01); *B29C 65/087* (2013.01);
(Continued)

(58) Field of Classification Search
CPC .......... A61F 13/15739; A61F 13/15593; A61F 13/15601; A61F 13/15609;
(Continued)

(56) References Cited

U.S. PATENT DOCUMENTS 1,588,018 A    6/1926  Fitz
3,993,532 A *  11/1976 McDonald ............ B29C 65/086
                                                156/580.2
(Continued)

FOREIGN PATENT DOCUMENTS

CA        1211745 A      9/1986
CN      102325513 A      1/2012
(Continued)

OTHER PUBLICATIONS

Machine translation of JP 11-291376 date unknown.*
(Continued)

*Primary Examiner* — John L Goff, II
(74) *Attorney, Agent, or Firm* — Armstrong Teasdale LLP

(57) ABSTRACT

An apparatus for fabricating an elastic nonwoven material generally includes a first bonding module and a second bonding module. The second bonding module is positionable in close proximity to the first bonding module. At least one of the first bonding module and the second bonding module has a face with a width dimension and a circumferential axis and is rotatable about a rotation axis. The face has a plurality of ridges. The ridges are positioned such that at least two adjacent ridges overlap along the circumferential axis.

18 Claims, 20 Drawing Sheets

(51) Int. Cl.
*A61F 13/15* (2006.01)
*B32B 5/02* (2006.01)
*B32B 37/14* (2006.01)
B32B 37/20 (2006.01)
B29L 31/48 (2006.01)
B32B 38/00 (2006.01)

(52) U.S. Cl.
CPC ........ *B29C 66/1122* (2013.01); *B29C 66/433* (2013.01); *B29C 66/7294* (2013.01); *B29C 66/8161* (2013.01); *B29C 66/81427* (2013.01); *B29C 66/81469* (2013.01); *B29C 66/8226* (2013.01); *B29C 66/8242* (2013.01); *B29C 66/8246* (2013.01); *B29C 66/83413* (2013.01); *B29C 66/8432* (2013.01); *B32B 5/022* (2013.01); *B32B 37/14* (2013.01); *A61F 2013/15861* (2013.01); *A61F 2013/15934* (2013.01); *B29C 66/876* (2013.01); *B29C 66/8762* (2013.01); *B29K 2995/0046* (2013.01); *B29L 2031/4878* (2013.01); *B32B 37/144* (2013.01); *B32B 37/206* (2013.01); *B32B 38/0004* (2013.01); *B32B 2555/02* (2013.01)

(58) Field of Classification Search
CPC .. A61F 2013/15861; A61F 2013/15869; A61F 13/49011; A61F 13/49012; A61F 13/49014; A61F 13/49015; A61F 13/49017; A61F 13/49019; A61F 13/4902; A61F 13/51464; A61F 2013/49025; A61F 2013/49026; A61F 2013/49028; B65H 57/04; B65H 57/16; B29C 43/24; B29C 59/04; B29C 65/08; B29C 65/081; B29C 65/082; B29C 65/083; B29C 65/085; B29C 65/086; B29C 65/087; B29C 65/088; B29C 66/433; B29C 66/81427; B29C 66/81431; B29C 66/81433; B29C 66/81435; B29C 66/81463; B29C 66/81465; B29C 66/81467; B29C 66/81469; B29C 66/8432; B29C 66/344; B29C 66/81429; B29C 66/83413
USPC ................ 156/73.1, 73.2, 290, 580.1, 580.2
See application file for complete search history.

(56) References Cited

U.S. PATENT DOCUMENTS

| | | |
|---|---|---|
| 4,146,416 A | 3/1979 | Goldman |
| 4,305,988 A | 12/1981 | Kocher |
| 4,333,978 A | 6/1982 | Kocher |
| 4,430,148 A | 2/1984 | Schaefer |
| 4,650,530 A | 3/1987 | Mahoney et al. |
| 4,713,132 A | 12/1987 | Abel et al. |
| 4,758,293 A | 7/1988 | Samida |
| 5,000,806 A | 3/1991 | Merkatoris |
| 5,325,555 A | 7/1994 | Whitley |
| 5,421,924 A | 6/1995 | Ziegelhoffer et al. |
| 5,525,175 A * | 6/1996 | Blenke ............ A61F 13/15593 156/161 |
| 5,530,979 A | 7/1996 | Whitley |
| 5,643,396 A | 7/1997 | Rajala et al. |
| 5,660,657 A | 8/1997 | Rajala et al. |
| 5,660,679 A | 8/1997 | Rajala et al. |
| 5,667,608 A | 9/1997 | Rajala et al. |
| 5,681,302 A | 10/1997 | Melbye et al. |
| 5,733,411 A | 3/1998 | Bett |
| 6,098,684 A | 8/2000 | Terawaki |
| 6,123,792 A | 9/2000 | Samida et al. |
| 6,165,298 A | 12/2000 | Samida et al. |
| 6,291,039 B1 | 9/2001 | Combe et al. |
| 6,309,487 B1 | 10/2001 | Herrin et al. |
| 6,340,782 B1 | 1/2002 | Kling et al. |
| 6,368,437 B1 | 4/2002 | Ziegelhoffer et al. |
| 6,574,944 B2 | 6/2003 | Capodieci |
| 7,059,103 B2 | 6/2006 | Ninomiya et al. |
| 7,060,142 B2 | 6/2006 | Yamamoto |
| 7,226,438 B2 | 6/2007 | Soga et al. |
| 7,299,600 B2 | 11/2007 | Caroli |
| 7,582,348 B2 | 9/2009 | Ando et al. |
| 7,642,398 B2 | 1/2010 | Jarpenberg et al. |
| 7,803,244 B2 * | 9/2010 | Siqueira ............ A61F 13/4902 156/229 |
| 7,905,871 B2 | 3/2011 | Mueller et al. |
| 8,458,993 B2 | 6/2013 | Schiebout et al. |
| 8,647,319 B2 | 2/2014 | Een et al. |
| 8,662,133 B2 | 3/2014 | Ninomiya et al. |
| 9,731,454 B2 | 8/2017 | Tam et al. |
| 10,213,348 B2 | 2/2019 | Gualtieri et al. |
| 2001/0008064 A1 | 7/2001 | Todd et al. |
| 2003/0089447 A1 | 5/2003 | Molee et al. |
| 2003/0111157 A1 | 6/2003 | Ehlert et al. |
| 2004/0166756 A1 | 8/2004 | Kurihara et al. |
| 2004/0219854 A1 | 11/2004 | Groitzsch et al. |
| 2005/0241773 A1 | 11/2005 | Schneider |
| 2006/0069373 A1 | 3/2006 | Schlinz et al. |
| 2006/0144904 A1 | 7/2006 | Mlinar et al. |
| 2006/0228969 A1 | 10/2006 | Erdman |
| 2006/0270302 A1 * | 11/2006 | Ando .................. A61F 13/4902 442/328 |
| 2010/0193138 A1 * | 8/2010 | Eckstein ........... A61F 13/15609 156/436 |
| 2011/0123773 A1 | 5/2011 | Lofink |
| 2012/0111483 A1 | 5/2012 | Schneider et al. |
| 2012/0186719 A1 | 7/2012 | Van Den Aker |
| 2013/0306226 A1 | 11/2013 | Zink et al. |
| 2014/0377506 A1 * | 12/2014 | Eckstein ........... A61F 13/49011 428/161 |
| 2016/0228305 A1 | 8/2016 | Gualtieri et al. |
| 2016/0288407 A1 * | 10/2016 | Ehlert ..................... B29C 65/08 |
| 2016/0331600 A1 | 11/2016 | Polidori et al. |
| 2017/0000662 A1 | 1/2017 | Schroer |
| 2017/0165131 A1 | 6/2017 | Varona et al. |
| 2018/0093444 A1 | 4/2018 | Begrow et al. |

FOREIGN PATENT DOCUMENTS

| | | |
|---|---|---|
| CN | 101868210 B | 9/2014 |
| CN | 104507436 A | 4/2015 |
| CN | 105142589 A | 12/2015 |
| CN | 106943236 A | 7/2017 |
| CN | 106999315 A | 8/2017 |
| CN | 108472182 A | 8/2018 |
| CN | 207804491 U | 9/2018 |
| EP | 22896 B1 | 4/1983 |
| EP | 685586 A3 | 2/1996 |
| EP | 943305 A1 | 9/1999 |
| EP | 0997123 A1 | 5/2000 |
| EP | 494941 B2 | 7/2002 |
| EP | 677284 B2 | 8/2005 |
| EP | 1609582 A1 | 12/2005 |
| EP | 1666178 A1 | 6/2006 |
| EP | 1876275 B1 | 1/2008 |
| EP | 1458553 B1 | 9/2009 |
| EP | 2186493 A1 | 5/2010 |
| EP | 2214614 A1 | 8/2010 |
| EP | 2412354 A1 | 2/2012 |
| EP | 2886089 A1 | 6/2015 |
| EP | 3056176 A1 | 8/2016 |
| EP | 3095589 A1 | 11/2016 |
| EP | 3429530 A1 | 1/2019 |
| FR | 2285975 A1 | 4/1976 |
| GB | 2378920 A | 2/2003 |
| IT | 1308626 B1 | 1/2002 |
| JP | 62225323 A | 10/1987 |
| JP | 8058007 A | 3/1996 |
| JP | 11291376 A * | 10/1999 |

(56) References Cited

FOREIGN PATENT DOCUMENTS

| | | |
|---|---|---|
| JP | 2000080552 A | 3/2000 |
| JP | 03212615 B2 | 9/2001 |
| JP | 03883530 B2 | 2/2007 |
| JP | 04322140 B2 | 8/2009 |
| JP | 04383883 B2 | 12/2009 |
| JP | 2010115424 A | 5/2010 |
| JP | 04535771 B2 | 9/2010 |
| JP | 2010220781 A | 10/2010 |
| JP | 2010220782 A | 10/2010 |
| JP | 2010220783 A | 10/2010 |
| JP | 05085239 B2 | 11/2012 |
| WO | 2004005018 A1 | 1/2004 |
| WO | 2009025975 A1 | 2/2009 |
| WO | 2009067055 A1 | 5/2009 |
| WO | 2010126415 A1 | 11/2010 |
| WO | 2013132404 A1 | 9/2013 |
| WO | 2014010365 A1 | 1/2014 |
| WO | 2014200102 A1 | 12/2014 |
| WO | 2016109514 A1 | 7/2016 |
| WO | 2018156817 A2 | 8/2018 |

OTHER PUBLICATIONS

ISR/WO of PCT/US2016/024617, Aurizon Ultrasonics, LLC., dated Jun. 30, 2016; 8 pages.
China Notification of First Office Action issued for related application 2016800275073 dated May 30, 2019; 13 pp.
PCT International Preliminary Report on Patentability for Application PCT/US17/54026 completed Nov. 19, 2018, 19 pages.
PCT International Search Report and Written Opinion for Application PCT/US17/54026 dated Nov. 30, 2017, 10 pages.

\* cited by examiner

APPARATUS FOR FABRICATING AN ELASTIC NONWOVEN MATERIAL

CROSS-REFERENCE TO RELATED APPLICATION

This application claims the benefit of U.S. Provisional Application No. 62/402,457 filed on Sep. 30, 2016, which is incorporated by reference herein in its entirety.

BACKGROUND

The present invention relates generally to elastic materials and, more particularly, to an apparatus for fabricating an elastic nonwoven material.

Elastic nonwoven materials are utilized in a variety of articles including personal care articles (e.g., adult briefs, baby diapers, child/adult pull-on pants, contour fit hygiene products, etc.) and medical garments (e.g., masks, caps, gowns, footwear, etc.).

At least some conventional methods for fabricating elastic nonwoven materials include adhesively bonding elastic strands between layers of nonwoven fabric when the elastic strands are in tension. Once the elastic strands are permitted to contract, the elastic strands gather areas of the nonwoven fabric such that the nonwoven fabric functions with an elastic property. However, the durability of elastic nonwoven materials made by these conventional methods is less than desirable because the adhesive bonds are prone to creep, which can result in a loss of elasticity over time. Moreover, it can be overly expensive to fabricate elastic nonwoven materials using these conventional methods. It would be useful, therefore, to provide a system for fabricating a more durable elastic nonwoven material in a more cost effective manner.

SUMMARY

In one embodiment, an apparatus for fabricating an elastic nonwoven material generally comprises a first bonding module and a second bonding module. The second bonding module is positionable in close proximity to the first bonding module. At least one of the first bonding module and the second bonding module has a face with a width dimension and a circumferential axis and is rotatable about a rotation axis. The face has a plurality of ridges. The ridges are positioned such that at least two adjacent ridges overlap along the circumferential axis.

In another embodiment, a method for fabricating an elastic nonwoven material generally comprises positioning a first bonding module in close proximity to a second bonding module. The method also includes positioning a nonwoven fabric and at least one elastic strand between the first bonding module and the second bonding module. The method further includes bonding the nonwoven fabric at a bond point to retain the at least one elastic strand on the nonwoven fabric. The method further includes cutting the at least one elastic strand to form a first cut and a second cut. The bond is between the first cut and the second cut such that the at least one elastic strand has free ends extending on two sides of the bond.

In yet another embodiment, a method for fabricating an elastic nonwoven material generally comprises positioning a first bonding module in close proximity to a second bonding module. At least one of the first bonding module and the second bonding module includes a face with a width dimension and a circumferential axis. The method also includes rotating at least one of the first bonding module and the second bonding module. The method further includes directing an elastic strand between the first bonding module and the second bonding module and along a curve relative to the circumferential axis. The method also includes bonding the elastic nonwoven material in a first region and a second region. At least a portion of the elastic strand is entrapped in the first region and at least a portion of the elastic strand is entrapped in the second region. The elastic strand extends along the curve between the first region and the second region.

In still another embodiment, an apparatus for fabricating an elastic nonwoven material including at least one elastic strand generally comprises a first bonding module and a second bonding module positionable in close proximity to the first bonding module. At least one of the first bonding module and the second bonding module has a face with a width dimension and a circumferential axis and is rotatable about a rotation axis. The face has a plurality of ridges. The first bonding module and the second bonding module are positioned to receive at least one elastic strand and a nonwoven material. The apparatus further includes a supply station configured to provide the at least one elastic strand. The at least one elastic strand is directed across the width dimension along a curve relative to the circumferential axis as the at least one of the first bonding module and the second bonding module is rotated.

BRIEF DESCRIPTION OF THE DRAWINGS

Corresponding reference characters indicate corresponding parts throughout the several views of the drawings.

DETAILED DESCRIPTION

Figure 1:
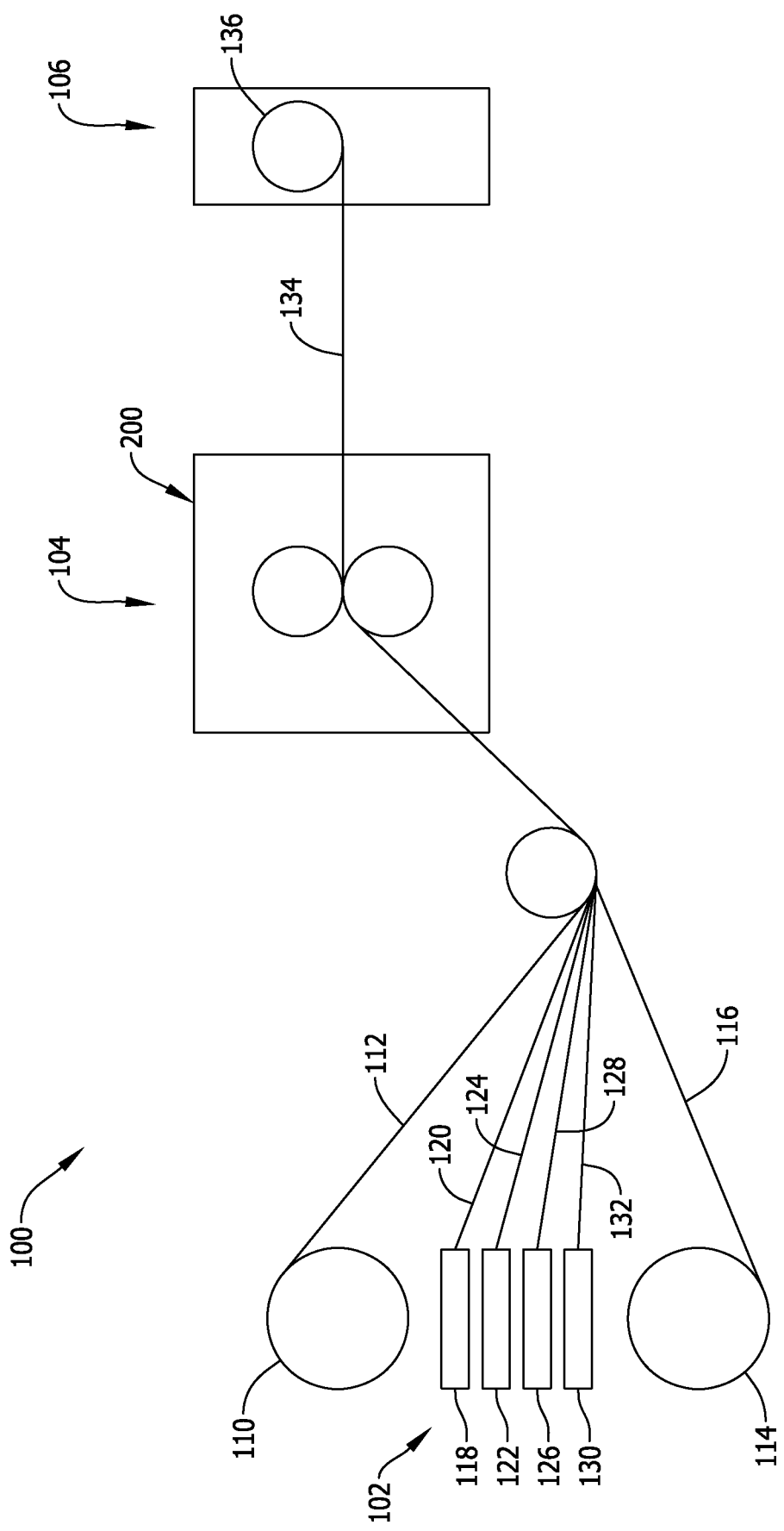
FIG. 1 is a schematic illustration of a system for fabricating an elastic nonwoven material.

Referring to the drawings, and in particular to FIG. 1, a system for fabricating an elastic nonwoven material is indicated generally by 100. The illustrated system 100 includes a supply station indicated generally by 102, a processing station indicated generally by 104, and a collection station indicated generally by 106. Other suitable stations are also contemplated without departing from the scope of this invention.

In the illustrated embodiment, the supply station 102 includes a plurality of supply rolls each containing a nonwoven fabric, namely a first supply roll 110 containing a first nonwoven fabric 112 and a second supply roll 114 containing a second nonwoven fabric 116. The supply station 102 also includes a plurality of supply spools each containing an elastic strand, namely a first supply spool 118 containing a first elastic strand 120, a second supply spool 122 containing a second elastic strand 124, a third supply spool 126 containing a third elastic strand 128, and a fourth supply spool 130 containing a fourth elastic strand 132. The elastic strands 120, 124, 128, 132 may have any suitable cross-sectional shape that facilitates enabling the elastic strands 120, 124, 128, 132 to function as described herein (e.g., a cross-sectional shape that is round, rectangular (e.g., relatively flat), square, etc.).

The illustrated processing station 104 includes a rotary ultrasonic bonding apparatus (indicated generally by 200) for bonding the elastic strands 120, 124, 128, 132 between the nonwoven fabrics 112, 116 to make an elastic nonwoven material 134, as set forth in more detail below. The collection station 106 may include any suitable device(s) for collecting the elastic nonwoven material 134 (e.g., a puller roll 136). In other embodiments, the supply station 102 may have any suitable quantity of supply rolls and supply spools having any suitable configuration that facilitates enabling the apparatus 200 to function as described herein.

FIGS. 2-7 are various embodiments of the rotary ultrasonic bonding apparatus 200. In the illustrated embodiments, the apparatus 200 has bonding modules, e.g., an anvil module 202 and a horn module 204, that cooperate to perform a bonding operation of the elastic strands 120, 124, 128, 132 between the nonwoven fabrics 112, 116 as set forth in more detail below.

In the illustrated embodiments, the horn module 204 includes a frame 206 on which are mounted a disc-like rotary horn 208, a motor 210 for driving rotation of the horn 208 via a suitable drive train 212, and a housing 214 which contains at least part of a vibration control unit (not shown) that causes the horn 208 to vibrate. The horn 208 has a face 216 with a substantially continuous contour (i.e., the horn face 216 has a contour that is substantially smooth (or uninterrupted) across its entire surface area). In other embodiments, the horn face 216 may have any suitable contour that facilitates enabling the horn 208 to function as described herein.

In some embodiments, the vibration control unit (while not illustrated) includes at least one booster (e.g., a drive booster and an integral booster) mechanically connected to a converter, which is electrically connectable to a generator. The converter is capable of converting high frequency electrical energy supplied by the generator into mechanical energy (or vibration) that is selectively transmitted to the horn 208 across the booster(s). The booster(s) are capable of modifying (i.e., increasing or decreasing) the vibration transmitted to the horn 208 from the converter, such that the horn 208 (particularly, the face 216 of the horn 208) vibrates while it rotates during a bonding operation, as set forth in more detail below. It is contemplated that the horn module 204 may have any suitable operational components arranged in any suitable manner that facilitates enabling the horn 208 to function as described herein.

In the illustrated embodiments, the anvil module 202 includes a frame 218 on which are mounted a disc-like rotary anvil 220 and a motor 222 for driving rotation of the anvil 220 via a suitable drive train 224. The anvil 220 has an annular face 226, the contour of which is not continuous (i.e., is interrupted) as set forth in more detail below. The anvil module 202 is positioned relative to the horn module 204 such that the anvil face 226 is rotatable in close proximity to the horn face 216, and vice versa, to facilitate ultrasonically bonding the elastic strands 120, 124, 128, 132 between the nonwoven fabrics 112, 116 when the elastic strands 120, 124, 128, 132 are held in tension across apparatus 200, as set forth in more detail below. As used herein, the term "close proximity" refers to when the anvil face 226 is either in contact with, or is minimally spaced apart from, the horn face 216 when the horn 208 is not ultrasonically vibrating.

In some embodiments, the apparatus 200 may be configured such that at least one of the anvil module 202 and the horn module 204 is displaceable relative to the other via a suitable displacement mechanism operable either: (A) when the system 100 is offline and the horn 208 is at rest (i.e., when the horn 208 is not rotating or vibrating); or (B) when the system 100 is online and the horn 208 is active (i.e., when the horn 208 is rotating and vibrating).

Figure 2:
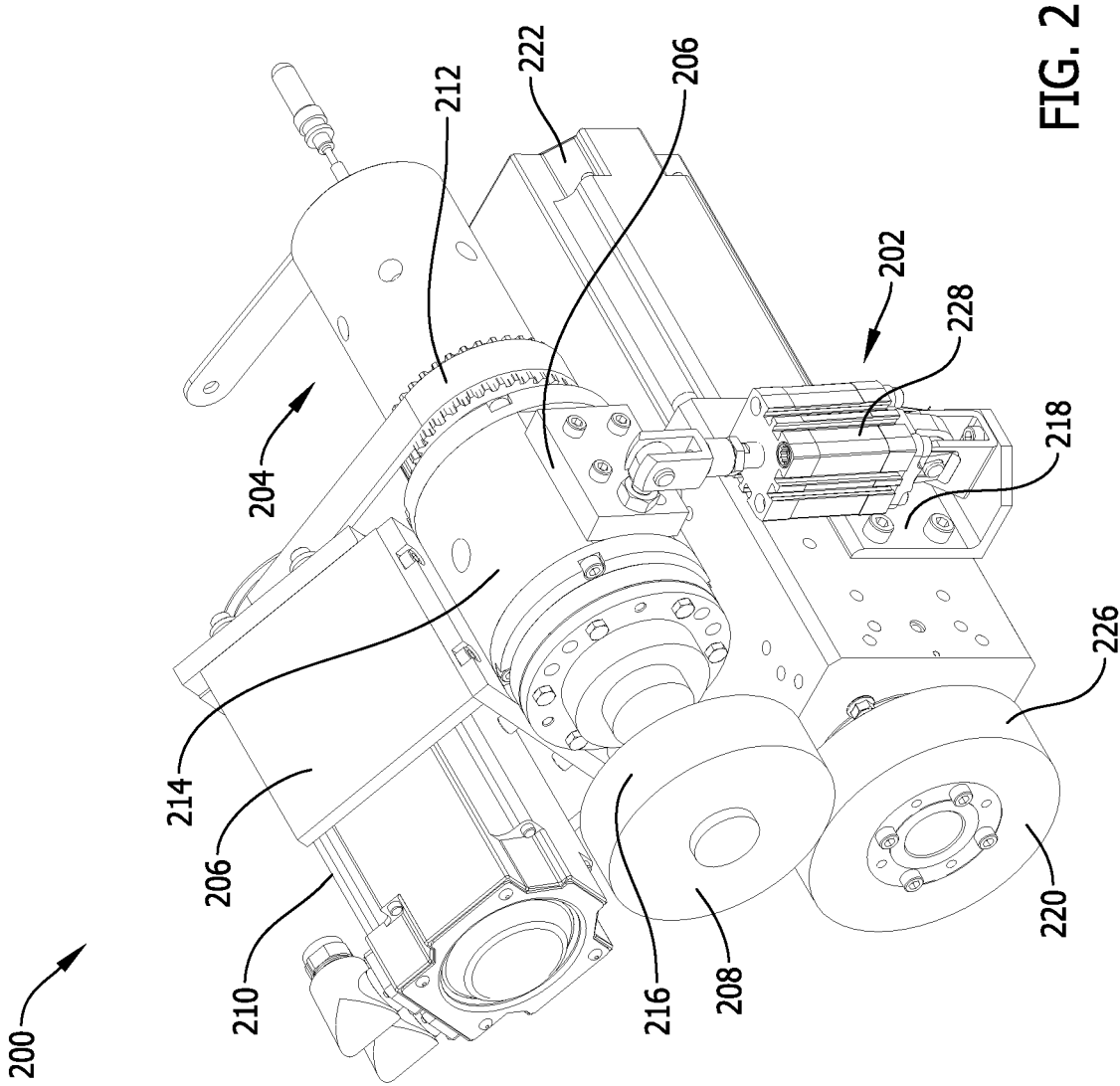
FIG. 2 is a perspective view of one embodiment of a rotary ultrasonic bonding apparatus for use in the system of FIG. 1.

With particular reference to the embodiment of FIG. 2, the apparatus 200 may be configured as a continuous-nip apparatus in which the horn module 204 is to be: (A) fixed in position relative to the anvil module 202 when the system 100 is online and the horn 208 is active; and (B) displaceable relative to the anvil module 202 when the system 100 is offline and the horn 208 is at rest. Such displacement is facilitated by a selectively actuatable pneumatic cylinder 228 (or other suitable linear actuator) that connects the frames 206, 218 to one another. In this manner, the spacing between the horn face 216 and the anvil face 226 is adjustable primarily for servicing the apparatus 200 when the system 100 is offline.

Figure 3:
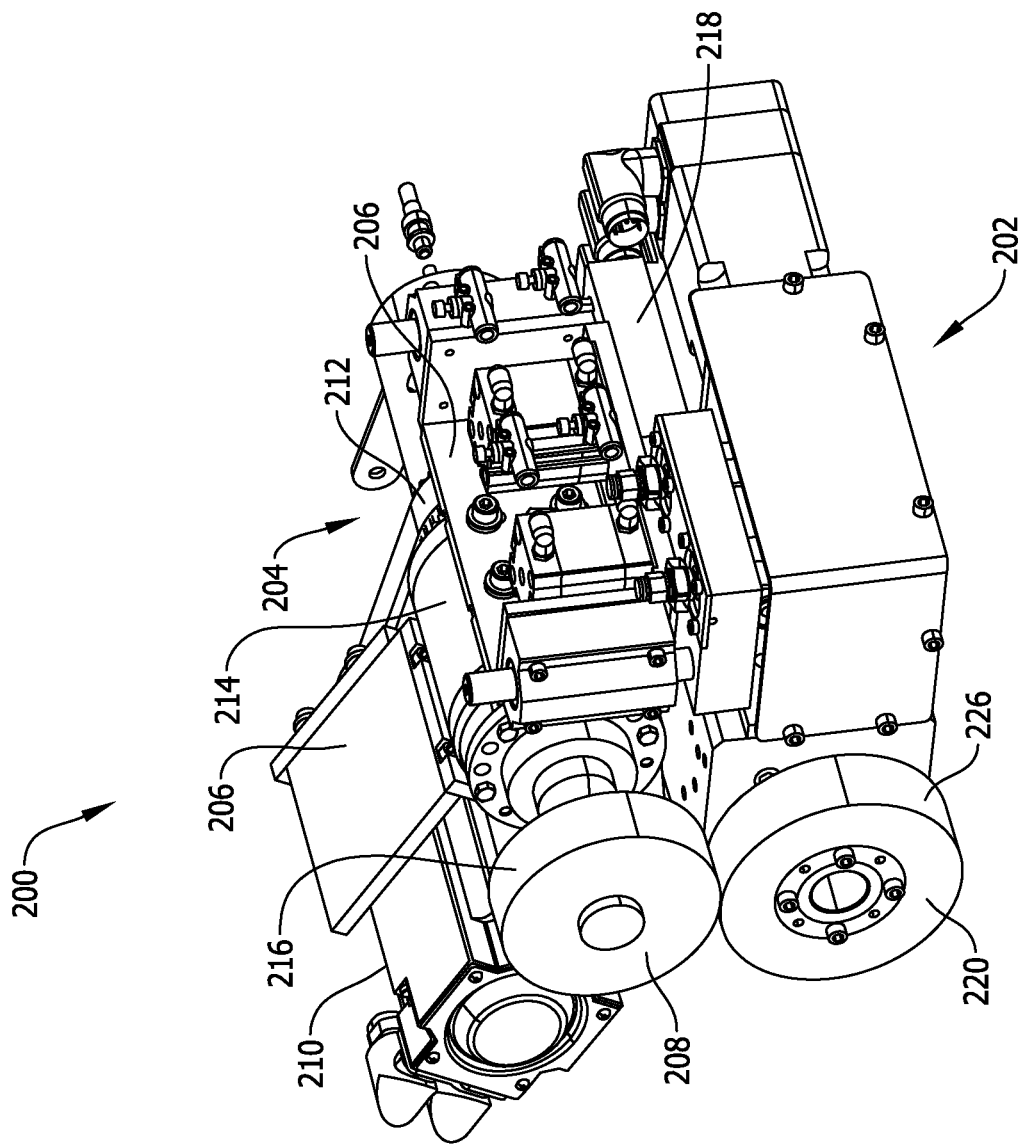
FIG. 3 is a perspective view of another embodiment of a rotary ultrasonic bonding apparatus for use in the system of FIG. 1.
Figure 4:
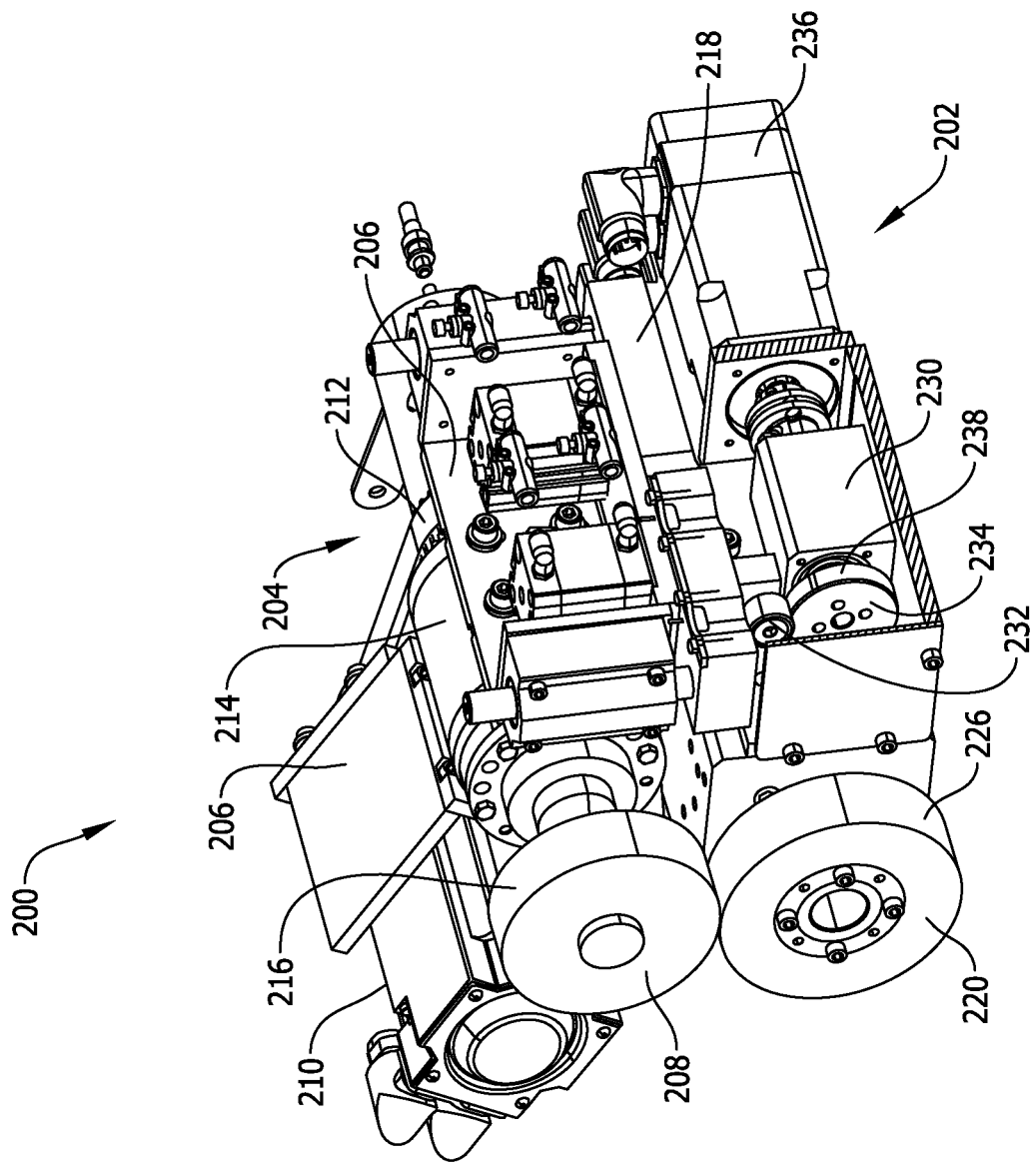
FIG. 4 is a partial cross-section of the apparatus of FIG. 3.

Referring now to the embodiment of FIGS. 3 and 4, the apparatus 200 may also be configured as an intermittent-nip apparatus in which the horn module 204 is displaceable relative to the anvil module 202 via a rotary camming device 230 when the system 100 is online and the horn 208 is active. The rotary camming device 230 has a follower 232 mounted to the horn module frame 206, and a cam wheel 234 mounted to the anvil module frame 218 and rotatable via a servomotor 236. The cam wheel 234 has an irregular camming surface 238 such that, when the cam wheel 234 is rotated via the servomotor 236, the follower 232 rides along the irregular camming surface 238 to cyclically displace the horn module frame 206 relative to the anvil module frame 218 at a predetermined frequency. In this manner, the spacing between the horn face 216 and the anvil face 226, and/or the frequency at which the horn face 216 contacts the anvil face 226, are selectively adjustable. Other displaceable arrangements of the horn module 204 and the anvil module 202 are also contemplated without departing from the scope of this invention.

Figure 5:
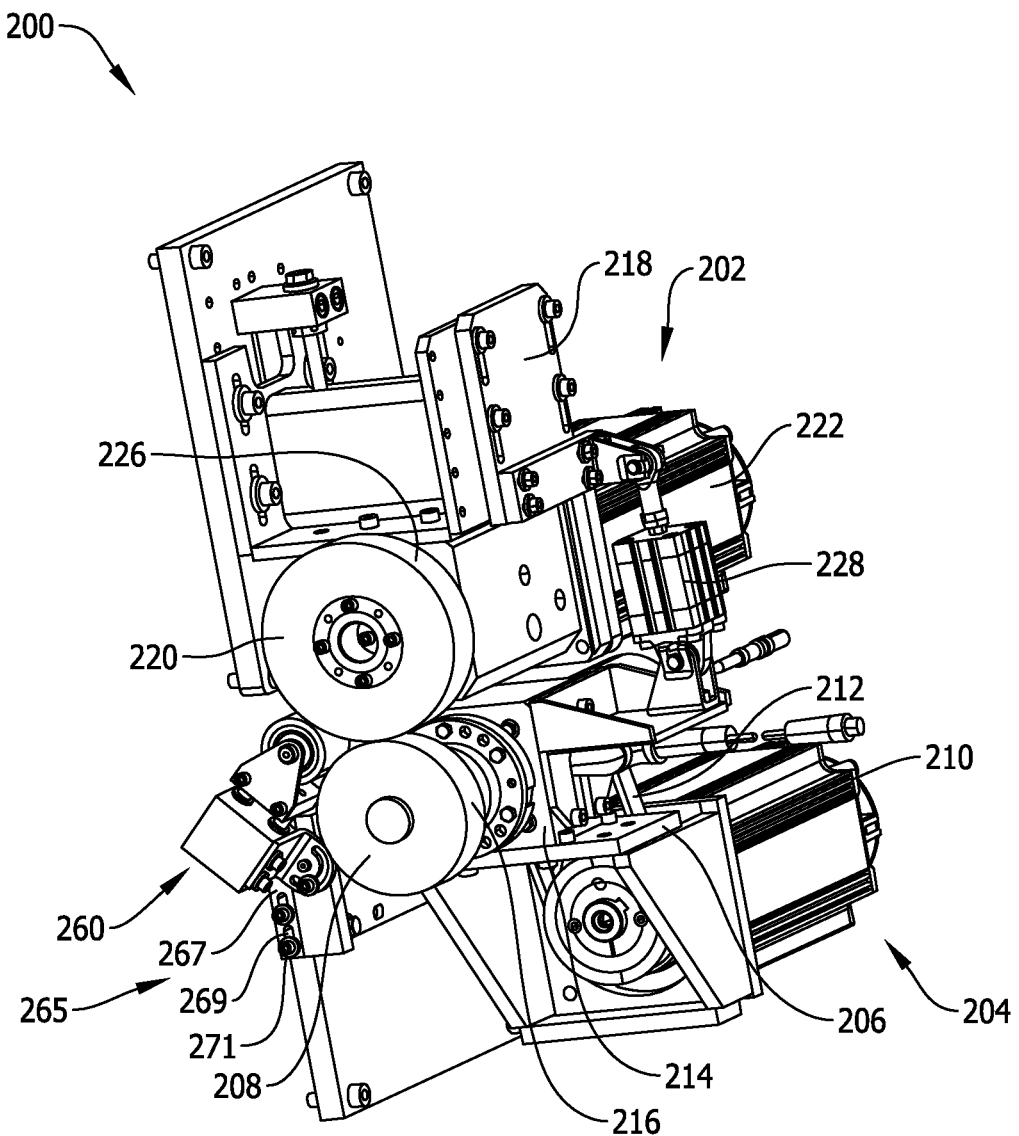
FIG. 5 is a perspective view of another embodiment of a rotary ultrasonic bonding apparatus for use in the system of FIG. 1.
Figure 6:
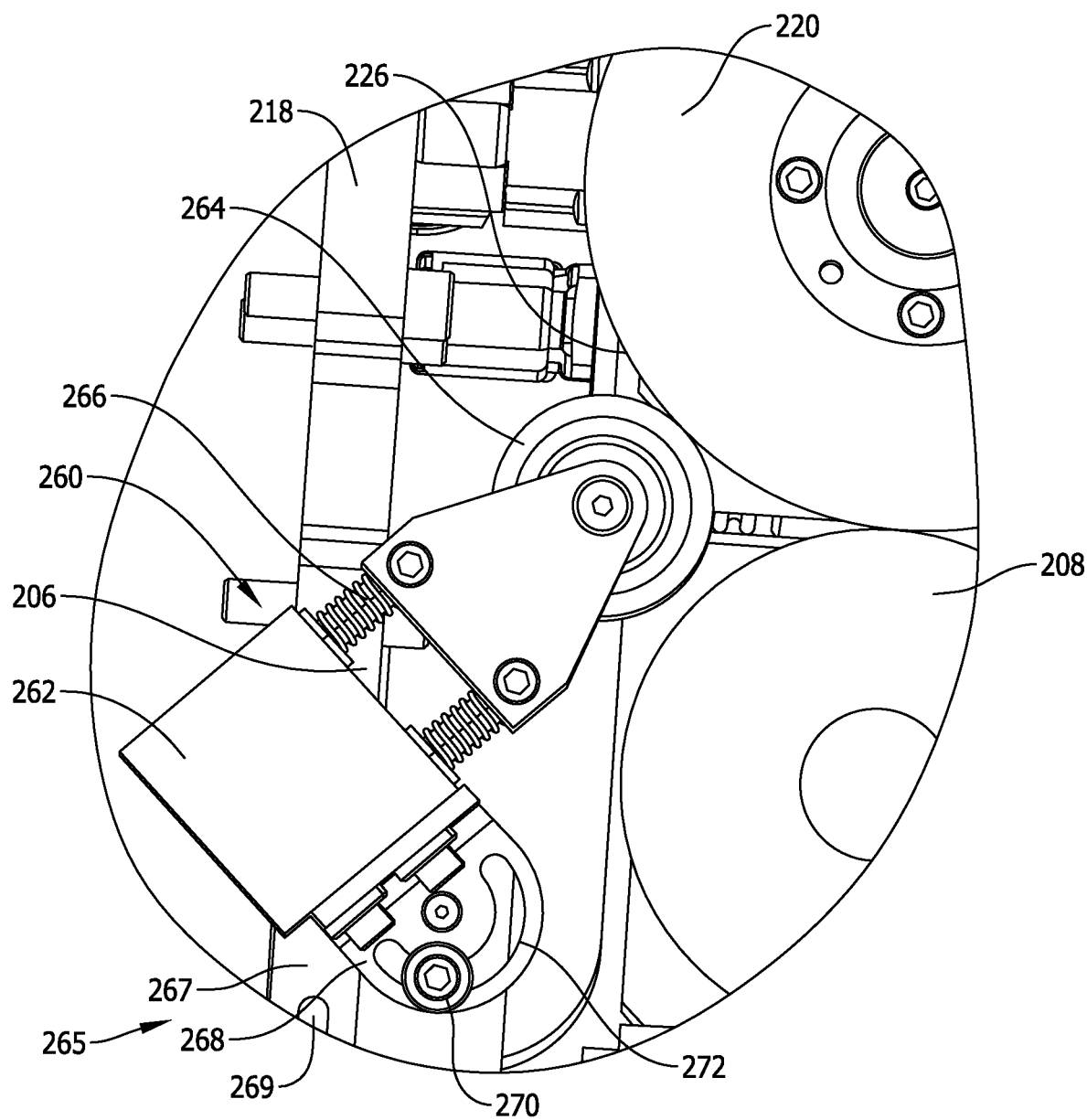
FIG. 6 is an enlarged side elevation view of a pinching device of the apparatus of FIG. 5.

As shown in the embodiment of FIGS. 5 and 6, the apparatus 200 may also include a pinching device 260. In the illustrated embodiment, the pinching device 260 includes a base 262 and a roller 264 floatingly mounted to the base 262 via at least one biasing element 266. The pinching device 260 also includes a bracket assembly 265 by which the base 262 and the roller 264 are mounted to at least one of the frame 206 and the frame 218, such that the base 262 and the roller 264 are adjustable in at least two degrees of freedom (as set forth in more detail below) in relation to the anvil 220 to facilitate use of the pinching device 260 in conjunction with anvils of different sizes.

The illustrated bracket assembly 265 includes a first bracket 267 and a second bracket 268. The first bracket 267 has at least one linear slot 269 through which a bolt 271 (which is fixed to either the frame 206 of the horn module 204 or the frame 218 of the anvil module 202) extends, and along which the bolt 271 is slidable, thereby rendering the first bracket 267 translatable relative to the frame 206 and/or 218. The second bracket 268 has at least one substantially arcuate slot 272 through which a bolt 270 (which is fixed to the first bracket 267) extends, and along which the bolt 270 is slidable, thereby rendering the second bracket 268 rotatable relative to the first bracket 267. The base 262 is mounted to the second bracket 268 such that the base 262 (and, therefore, the roller 264) are rotatably adjustable in a first degree of freedom via rotation of the second bracket 268, and are translatably adjustable in a second degree of freedom via translation of the first bracket 267.

The position of the base 262 and, therefore, the roller 264 are fixable via the bolt 270 and the bolt 271 to achieve a desired pinching contact between the roller 264 and the anvil face 226. For example, in the illustrated embodiment, the base 262 and the roller 264 are oriented such that the biasing element 266 applies a biasing force oriented substantially perpendicular to a rotation axis of the anvil 220 when viewed as in FIG. 6. In other embodiments, the pinching device 260 may have any suitable components arranged and movable (e.g., translatable and/or rotatable) in any suitable manner that facilitates enabling the pinching device 260 to perform the pinching action described herein (e.g., on any suitable bracket assembly that facilitates enabling the base 262 and the roller 264 to be adjustable in at least two degrees of freedom such as, for example, two translating degrees of freedom, or one translating degree of freedom and one rotating degree of freedom).

In this manner, the pinching device 260 limits the snap-back potential of elastic strands 120, 124, 128, 132 that become severed between horn 208 and anvil 220 during a bonding operation. More specifically, the pinching device 260 effectively catches broken elastic strand(s) 120, 124, 128, 132 between the roller 264 and the anvil 220 to prevent the broken elastic strands 120, 124, 128, 132 from snapping back to their respective supply spool(s) 118, 122, 126, 130. Moreover, because the roller 264 rotates by virtue of being in contact with anvil 220, any broken elastic strands 120, 124, 128, 132 are caught at the interface of roller 264 and anvil 220 and are automatically fed back into the interface between horn 208 and anvil 220. As such, the pinching device 260 serves as a self-threading device for broken elastic strands 120, 124, 128, 132.

Figure 7:
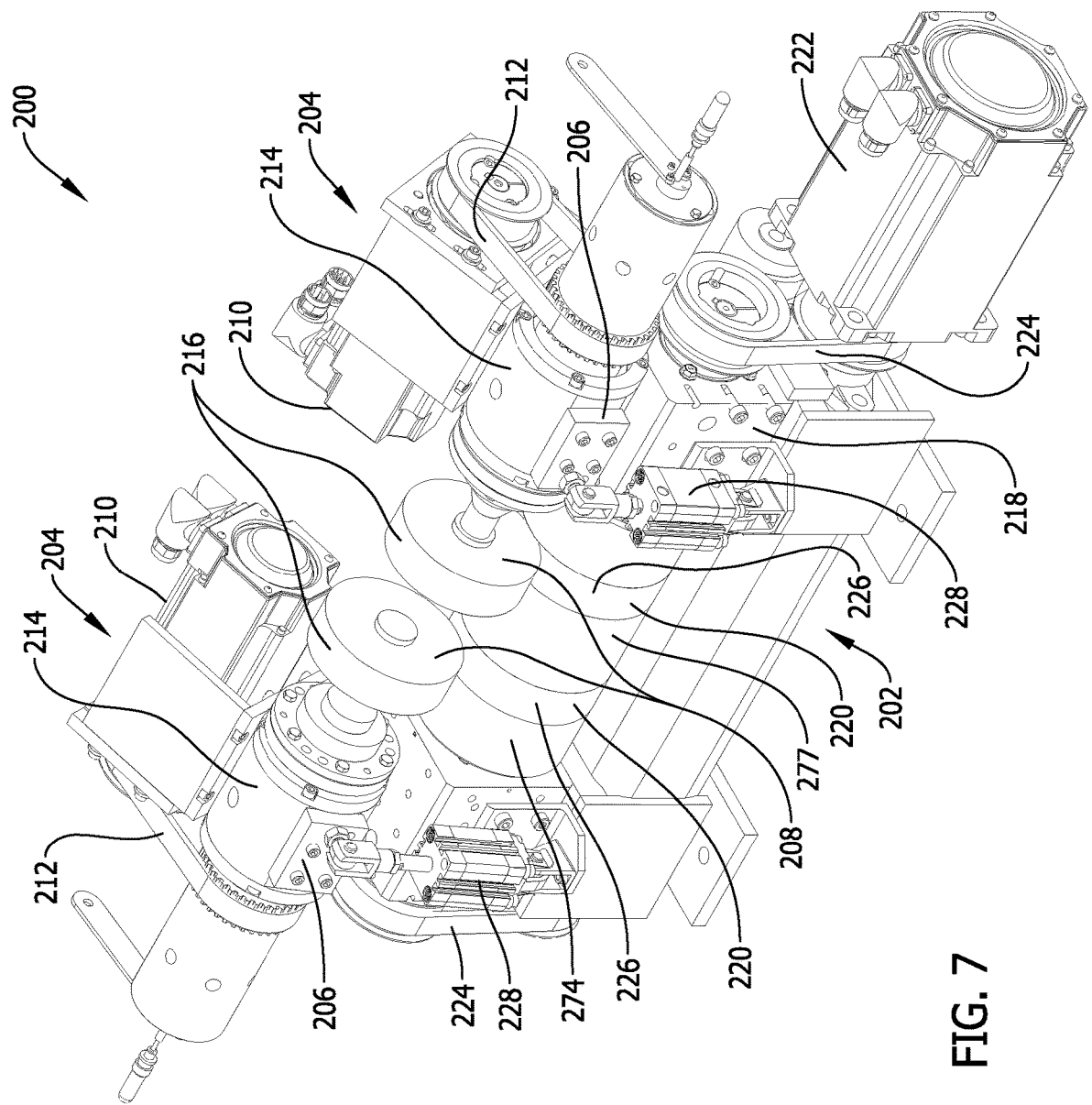
FIG. 7 is a perspective view of yet another embodiment of a rotary ultrasonic bonding apparatus for use in the system of FIG. 1.

Notably, the apparatus 200 may have any suitable quantity of anvil modules 202 and/or horn modules 204 that cooperate with one another to facilitate enabling the apparatus 200 to function as described herein. For example, as illustrated in the embodiment of FIG. 7, the apparatus 200 may be configured with an anvil drum 274 in which a pair of anvils 220 are positioned such that the drum 274 has a pair of predefined, annular faces 226 that are spaced apart from one another. In this manner, the horn 208 of a separate horn module 204 is dedicated to each such anvil face 226, thereby facilitating a bonding operation on confined regions of larger nonwoven fabrics on which only partial elasticity is desired (e.g., segments of these larger nonwoven fabrics on which elasticity is not desired may move along non-contact regions 277 of the drum 274 to avoid interaction with the associated horn(s) 208).

To facilitate minimizing the occurrence of elastic strands 120, 124, 128, 132 being cut between the horn 208 and the anvil 220 during a bonding operation, it is desirable to effectively hold the elastic strands 120, 124, 128, 132 in place within notches of the anvil face 226 while the nonwoven fabrics 112, 116 are bonded together between the horn 208 and the anvil 220. At least the following operational parameters contribute to minimizing the occurrence of elastic strands 120, 124, 128, 132 being cut during a bonding operation: (A) the specific energy source (e.g., the amplitude of vibration of the horn 208 and its pressure when contacting the anvil 220); (B) the energy director (e.g., the geometry of the anvil face 226); and (C) the material system (e.g., the decitex and tension of the elastic strands 120, 124, 128, 132, and the basis weight of the nonwoven fabrics 112, 116).

Figure 8:
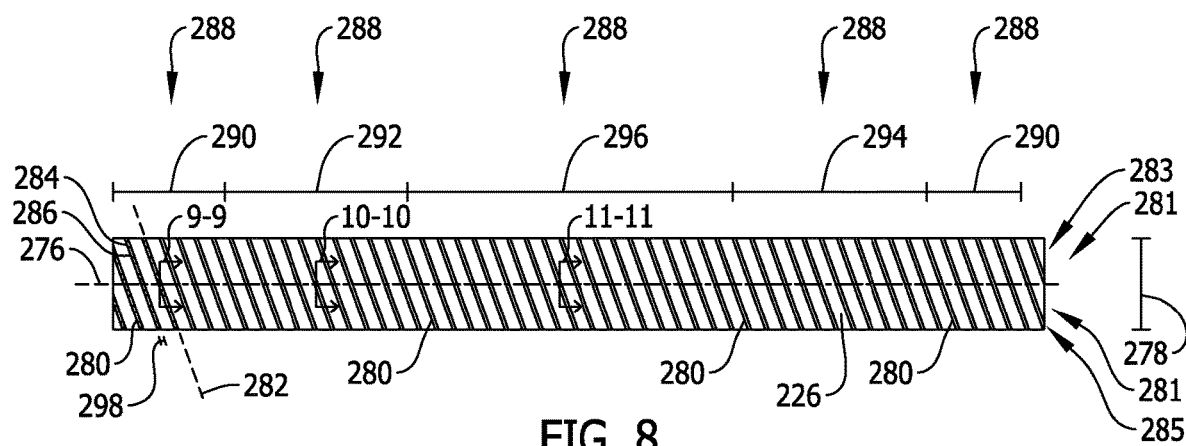
FIG. 8 is a laid-flat illustration of an annular face of one embodiment of an anvil for use in the apparatuses of FIGS. 2-7.

With respect to one such parameter (i.e., the geometry of the anvil face 226), FIG. 8 is a laid-flat illustration of an embodiment of the anvil face 226 of the apparatus 200. In the illustrated embodiment, the anvil face 226 has a circumferential axis 276 and a width dimension 278 oriented perpendicular to the axis 276. The contour of the anvil face 226 is irregular (i.e., not continuous) along the axis 276, in that the anvil face 226 defines a plurality of circumferentially spaced ridges 280. For example, in some embodiments, each adjacent pair of ridges 280 may have a spacing (or pitch) measured along the axis 276 of between about 0.10 inches and about 1.00 inches (e.g., between about 0.20 inches and about 0.50 inches). While all adjacent pairs of ridges 280 on the anvil face 226 are substantially equally spaced apart from one another in the illustrated embodiment, it is contemplated that the spacing between adjacent pairs of ridges 280 may vary along the axis 276 in other embodiments.

Figure 9:
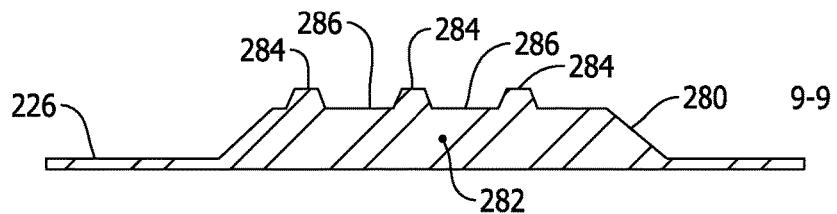
FIG. 9 is a cross-section, taken along plane 9-9 of FIG. 8, of one embodiment of a ridge defined by the anvil face of FIG. 8.

In the illustrated embodiment, each ridge 280 extends substantially linearly across the circumferential axis 276 so as to span substantially the entire width dimension 278 of the anvil face 226. Each ridge 280 has an extension axis 282 oriented oblique to the circumferential axis 276. As illustrated in FIG. 9, each ridge 280 includes a plurality of lands 284 spaced along its extension axis 282 such that each adjacent pair of lands 284 is spaced apart by (or flank) a notch 286. While the lands 284 and notches 286 are illustrated on only a select few of the ridges 280 in FIG. 8, it is understood that all ridges 280 of anvil face 226 likewise have a set of lands 284 and notches 286 along their respective extension axes 282. Notably, adjacent ones of the lands 284 of each ridge 280 are shaped such that the corresponding notch 286 defined therebetween is oriented substantially parallel to the circumferential axis 276 (i.e., the ridges 280 and the notches 286 each have a lengthwise dimension 298 that is oriented substantially parallel to the circumferential axis 276 in the illustrated embodiment).

In some embodiments, the anvil face 226 may be configured for a continuous entrapment bonding operation. More specifically, in such embodiments, each of the ridges 280 has at least one notch 286 that is aligned in the width dimension 278 with a corresponding notch 286 of each other ridge 280, and the lands 284 that flank each aligned notch 286 are spaced to create widthwise adjacent bonds in the nonwoven fabrics 112, 116 that are close enough together in the width dimension 278 to permanently hold the associated elastic strand 120, 124, 128, 132 in tension therebetween. As a result, after the bonding operation is complete and the nonwoven fabrics 112, 116 are removed from the system 100, at least one of the elastic strands 120, 124, 128, 132 is subsequently permitted to contract between circumferentially adjacent rows of bonds, but not between the widthwise adjacent bonds through which the elastic strand(s) 120, 124, 128, 132 extend. The entrapment bonding operation is therefore said to be continuous in the sense that at least one of the elastic strands 120, 124, 128, 132 is caused to be permanently held in tension between each widthwise adjacent pair of bonds through which it extends.

In one embodiment of a continuous entrapment configuration of the anvil face 226, the lands 284 and the notches 286 of each ridge 280 have sizes (and, therefore, spacings) relative to one another that are substantially the same as those of all other ridges 280 on the anvil face 226. The notches 286 are generally U-shaped or generally V-shaped, such that the sidewalls of the lands 284 that flank each notch 286 may, when viewed from a cross-sectional profile of the notch 286 as shown in FIG. 9, form a wedge angle therebetween of between about 1° and about 140° (e.g., between about 60° and about 100°. Notches 286 of other shapes are also contemplated. For example, in some embodiments, the sidewalls may form an angle of about 0° (i.e., the sidewalls may be about parallel to one another).

In one particular embodiment, if the elastic strands 120, 124, 128, 132 have a decitex of between about 300 and about 1240, and if the nonwoven fabrics 112, 116 have a grammage (gsm) of between about 8 and 30, the lands 284 may have lengths at their peaks of between about 0.010 inches and about 0.25 inches (e.g., between about 0.030 inches and about 0.060 inches), and widths at their peaks of between about 0.008 inches and about 0.050 inches (e.g., between about 0.010 inches and about 0.030 inches). Also, in that example, the notches 286 may have: depths measured from the peaks of their flanking lands 284 of between about 0.002 inches and about 0.040 inches (e.g., between about 0.004 inches and about 0.02 inches); widths measured at the peaks of their flanking lands 284 of between about 0.006 inches and about 0.016 inches (e.g., between about 0.008 inches and about 0.015 inches); and widths measured at their bases of between about 0.002 inches and about 0.02 inches (e.g., between about 0.004 inches and about 0.015 inches).

By providing the lands 284 and the notches 286 with the dimensions of the above example, the anvil face 226 facilitates improved gripping of the elastic strands 120, 124, 128, 132 in the notches 286 and, therefore, facilitates preventing the elastic strands 120, 124, 128, 132 from withdrawing out of the notches 286 to reduce the occurrence of severed elastic strands 120, 124, 128, 132. Other suitable sizes for the lands 284 and the notches 286 are also contemplated without departing from the scope of this invention.

In other embodiments, the anvil face 226 may be configured for an intermittent entrapment bonding operation, such that the lands 284 that flank at least one of the notches 286 are spaced to create widthwise adjacent bonds in the nonwoven fabrics 112, 116 that are not close enough together in the width dimension 278 to permanently hold the associated elastic strand 120, 124, 128, 132 in tension therebetween. As a result, after the bonding operation is complete and the nonwoven fabrics 112, 116 are removed from the system 100, the corresponding elastic strand 120, 124, 128, 132 is subsequently permitted to contract between the widthwise adjacent bonds through which it extends such that its tension between those widthwise adjacent bonds is substantially relieved. The entrapment bonding operation is therefore said to be intermittent in the sense that at least one of the elastic strands 120, 124, 128, 132 is not permanently held in tension between all pairs of widthwise adjacent bonds through which it extends.

In one embodiment of an intermittent entrapment configuration of the anvil face 226, the anvil face 226 may be provided with a plurality of distinct circumferential regions 288 such that a dimension of a notch 286 (and, therefore, the lands 284 that flank it) on a ridge 280 in at least one circumferential region 288 is different than a dimension of a widthwise aligned notch 286 (and, therefore, the lands 284 that flank it) on a ridge 280 in at least one other circumferential region 288.

Figure 10:
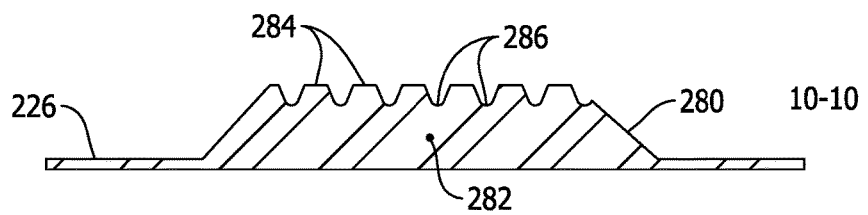
FIG. 10 is a cross-section, taken along plane 10-10 of FIG. 8, of another embodiment of a ridge defined by the anvil face of FIG. 8.

For example, each ridge 280 in a plurality of first circumferential regions 290, 296 may have at least one notch 286 that is sized differently as compared to at least one notch 286 that is widthwise aligned therewith on ridges 280 in a plurality of second circumferential regions 292, 294 interspaced between the first circumferential regions 290, 296. In this example, within the first circumferential regions 290, 296, the notches 286 may be sized with larger widths (like in FIG. 9) such that the elastic strands 120, 124, 128, 132 do not later become entrapped across (i.e., are later permitted to slip between) the widthwise adjacent bonds created at widthwise adjacent lands 284 on ridges 280 in these first circumferential regions 290, 296. Whereas, within the second circumferential regions 292, 294, the notches 286 may be sized with smaller widths (like in FIG. 10) such that the elastic strands 120, 124, 128, 132 later become entrapped across (i.e., are not later permitted to slip between) the widthwise adjacent bonds created at widthwise adjacent lands 284 on ridges 280 in the second circumferential regions 292, 294.

More specifically, in this example, at least one ridge 280 in each second circumferential region 292, 294 may have its notches 286 sized in the manner set forth above for the continuous entrapment example, while at least one ridge 280 in each first circumferential region 290, 296 may have its notches 286 sized with a width (as measured at the peaks of its flanking lands 284) of between about 0.010 inches and about 0.25 inches (e.g., between about 0.030 inches and about 0.060 inches in some embodiments; or about 0.035 inches in one particular embodiment). Thus, adequate slippage of the elastic strands 120, 124, 128, 132 across at least one ridge 280 in each first circumferential region 290, 296 is facilitated, especially when the elastic strands 120, 124, 128, 132 have a decitex of between about 300 and about 1240, and when the nonwoven fabrics 112, 116 have a grammage (gsm) of between about 8 and 30.

Figure 11:
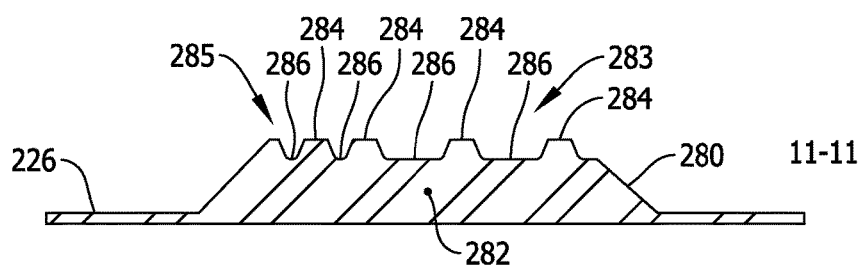
FIG. 11 is a cross-section, taken along plane 11-11 of FIG. 8, of yet another embodiment of a ridge defined by the anvil face of FIG. 8.

In both a continuous entrapment configuration and an intermittent entrapment configuration, the anvil face 226 may have a plurality of distinct widthwise segments 281, wherein each widthwise segment 281 has lands 284 and/or notches 286 of comparatively different sizes. For example, in one particular embodiment illustrated by FIG. 11, the anvil face 226 may have a first widthwise segment 283 with lands 284 that define notches 286 of a first width to suit elastic strands 120, 124, 128, 132 of a first decitex, and a second widthwise segment 285 with lands 284 that define notches 286 of a second width that is less than the first width to suit elastic strands 120, 124, 128, 132 of a second decitex that is less than the first decitex. Thus, each widthwise segment 281, no matter whether it is configured for continuous or intermittent entrapment, may be sized to accommodate elastic strands 120, 124, 128, 132 of different sizes.

Figure 12:
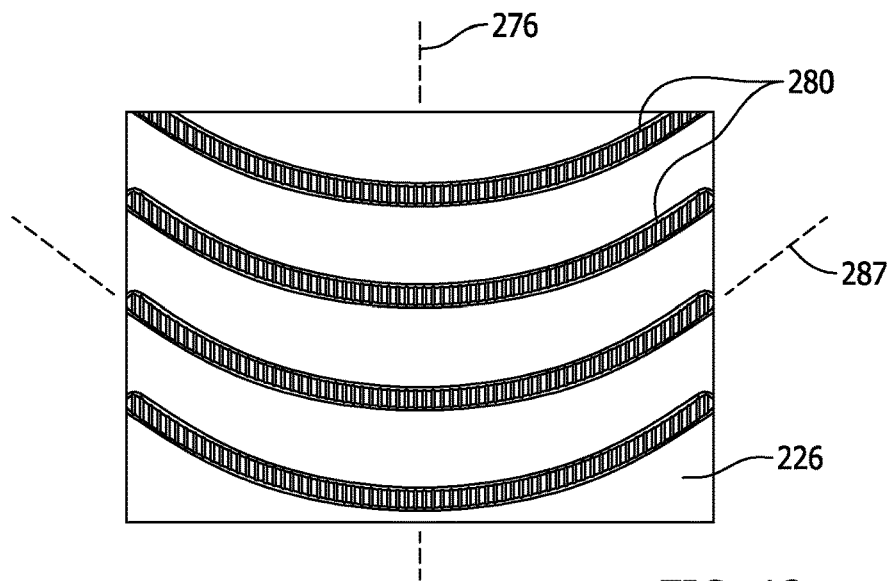
FIG. 12 is a laid-flat illustration of a portion of an annular face of another embodiment of an anvil for use in the apparatuses of FIGS. 2-7.
Figure 13:
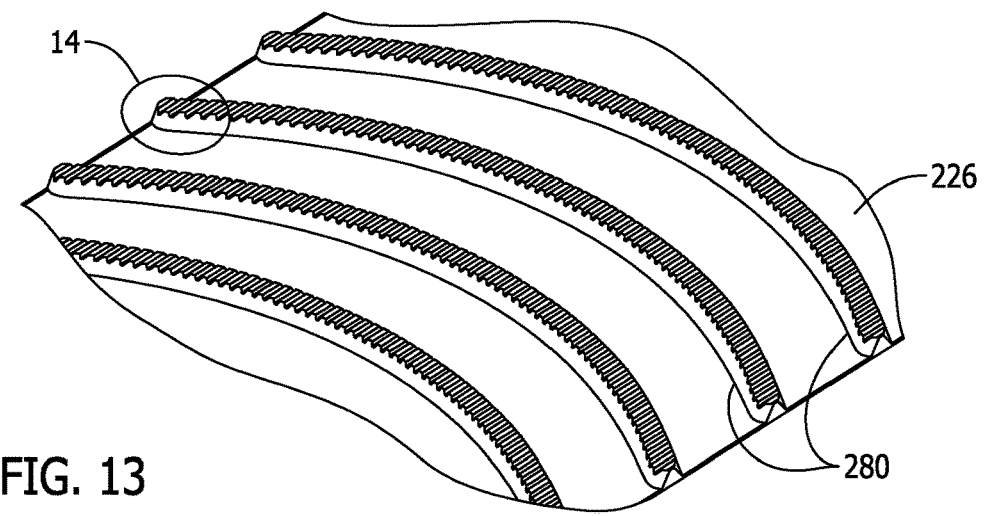
FIG. 13 is a perspective view of the portion of the annular face of FIG. 12.
Figure 14:
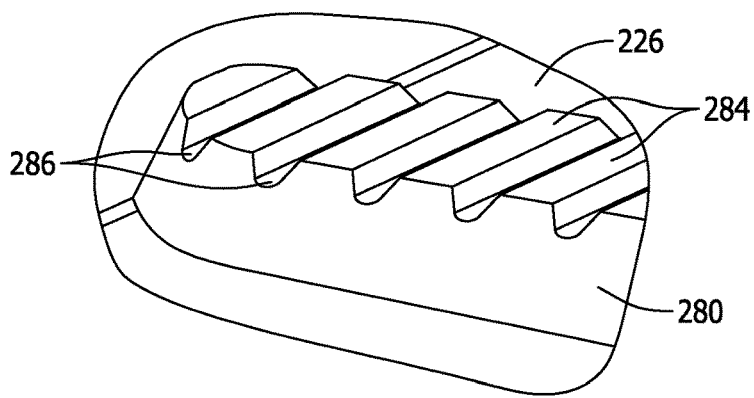
FIG. 14 is an enlarged segment of the perspective view of FIG. 13 taken within area 14 of FIG. 13.

In yet other embodiments, the anvil face 226 may have ridges 280 that extend non-linearly across the circumferential axis 276. For example, in one particular embodiment illustrated by FIGS. 12-14, the anvil face 226 may define a plurality of ridges 280 each with a curvilinear axis (e.g., a substantially arcuate axis 287). Notably, these embodiments with non-linear ridges 280 may have the same dimensions for the lands 284 and the notches 286 as for the substantially linearly extending ridges 280 set forth above, including the same dimensional variations amongst circumferential and widthwise regions 288, 281 as is set forth above with respect to the substantially linearly extending ridges 280.

Figure 15:
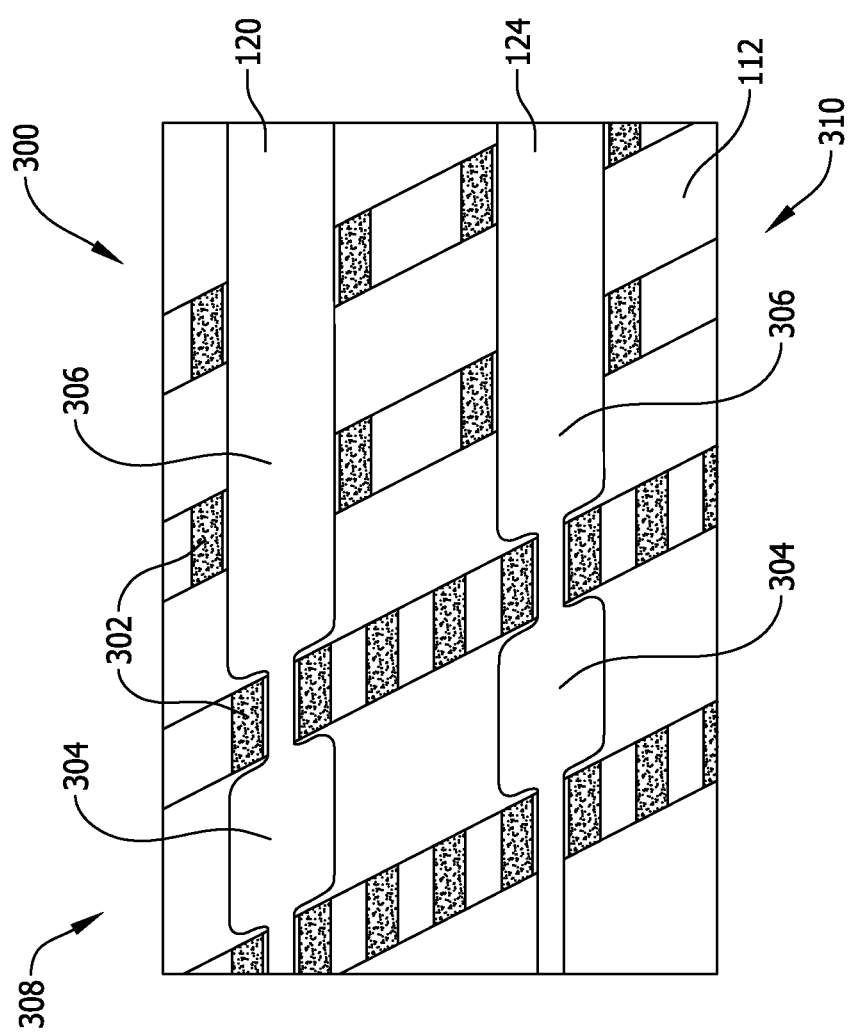
FIG. 15 is a schematic illustration of an elastic nonwoven material fabricated using an embodiment of the system of FIG. 1.

FIG. 15 illustrates an elastic nonwoven material 300 fabricated using the system 100. In the illustrated embodiment, an intermittent entrapment bonding process was performed on the nonwoven fabrics 112, 116 (with elastic strands 120, 124 sandwiched therebetween) using one of the embodiments of the apparatus 200 set forth above. The embodiment of the anvil 220 utilized to fabricate the material 300 has an anvil face 226 with notches 286 that vary in size across circumferential regions 288 as set forth in some of the embodiments above. In this manner, with the nonwoven fabrics 112, 116 and the elastic strands 120, 124 held in tension across the apparatus 200, the horn face 216 and the anvil face 226 created bonds 302 at locations corresponding to the lands 284 of the anvil face 226.

Once the bonded nonwoven fabrics 112, 116 (and the elastic strands 120, 124 sandwiched therebetween) were subsequently removed from the system 100, the tension in the elastic strands 120, 124 was partly relieved such that segments of each elastic strand 120, 124 were permitted to contract to create material 300. More specifically, a first segment 304 of each elastic strand 120, 124 became entrapped between adjacent rows of bonds 302 that corresponded to the ridges 280 which defined notches 286 of smaller widths. Whereas, a second segment 306 of each elastic strand 120, 124 was permitted to slip across widthwise adjacent bonds 302 in rows that corresponded to the ridges 280 which defined notches 286 of larger widths. In this manner, the nonwoven fabrics 112, 116 were caused to gather in areas 308 of the material 300 that have widthwise adjacent bonds 302 of closer spacing (but not in areas 310 that have widthwise adjacent bonds 302 of greater spacing) to effectively provide the material 300 with an elastic property. Notably, if a continuous entrapment operation had been utilized instead of an intermittent entrapment operation, the material 300 would not have second segments 306 that are permitted to slip, but would instead only have first segments 304 such that the nonwoven fabrics 112, 116 would gather along the entire material 300.

FIGS. 16-24 are laid-flat illustrations of portions of annular faces 226 of embodiments of anvils 220 for use in the apparatuses 200 shown in FIGS. 2-7. The anvil faces 226 shown in FIGS. 16-24 include ridges 280 arranged in patterns that enable the anvil 220 and the horn 208 to provide continuous running contact during operation of the apparatus 200. As used herein, the term "continuous running contact" means that the annular face 226 of the anvil 220 is configured to receive forces from the horn 208 substantially continuously throughout operation of the apparatus 200. In the example embodiments, continuous running contact allows the anvil 220 and the horn 208 to experience substantially uniform forces throughout operation. Thus, the energy required to operate the apparatus 200 is reduced. In addition, wear of the horn 208 and the anvil 220 is reduced in comparison to known systems. Moreover, vibration and/or noise associated with operation of the apparatus 200 can be reduced.

Embodiments of the of the annular faces 226 may allow for increased spacing between attachment points in the elastic nonwoven material and allow more independent movement of individual elastic strands 120, 124, 128, 132 relative to the elastic nonwoven fabric. Accordingly, the elastic strands 120, 124, 128, 132 may have increased elastic characteristics and function similar to an unattached elastic strand. For example, the annular faces 226 may allow for attachment points to be spaced apart by a distance up to about 150 mm or in a range of about 100 mm to about 150 mm. In alternative embodiments, the elastic strands 120, 124, 128, 132 may have any attachment points that allow the elastic strands to function as described herein. In some embodiments, bond points may be used between attachment points to guide the elastic strands 120, 124, 128, 132 without attaching the strands. In addition, the bond points may be used to provide continuous running contact.

Figure 16:
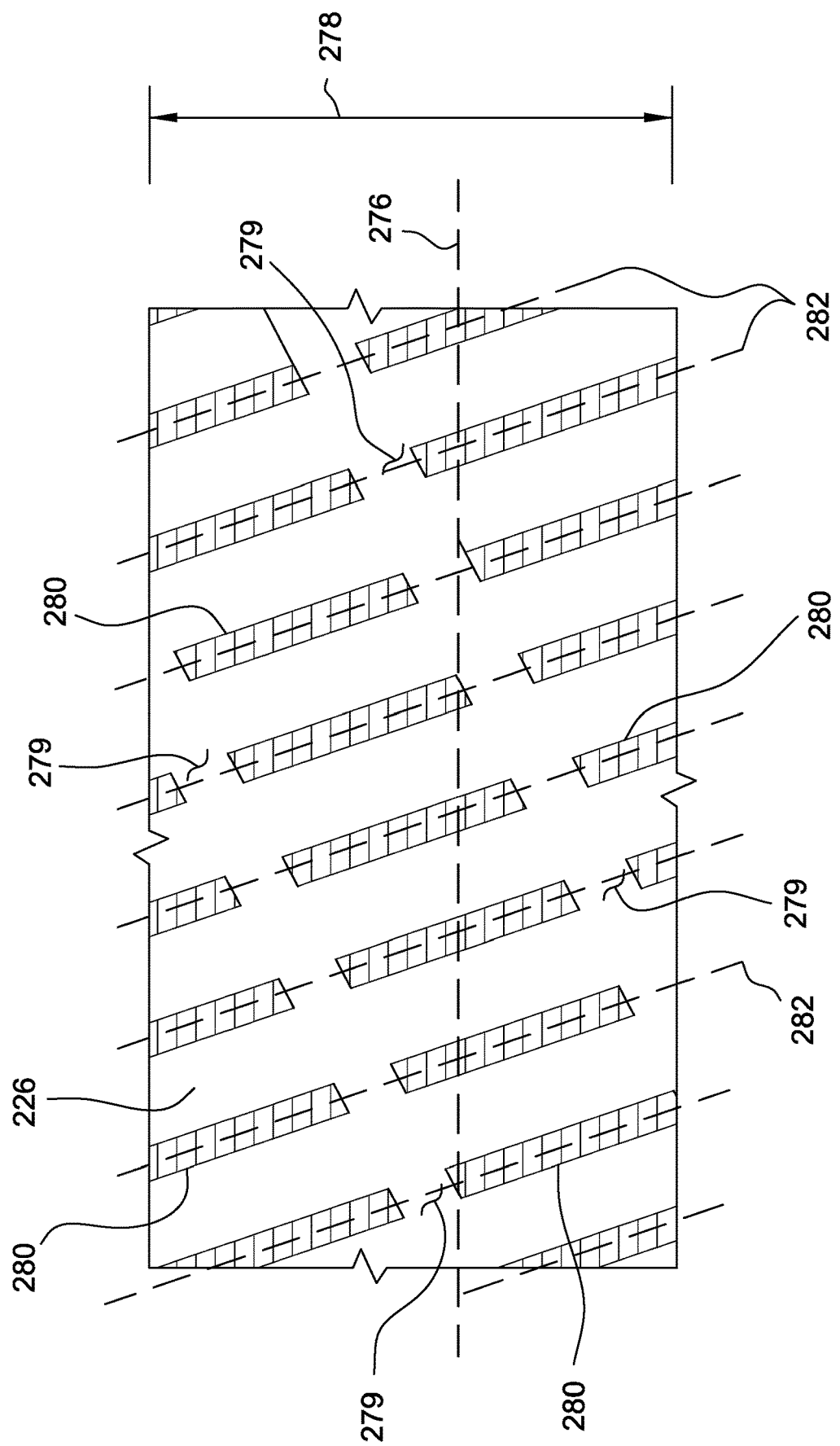
FIG. 16 is a laid-flat illustration of a portion of an annular face of yet another embodiment of an anvil for use in the apparatuses of FIGS. 2-7, the annular face including discontinuous ridges.

FIG. 16 is a laid-flat illustration of an embodiment of the anvil face 226 including ridges 280 and gaps 279. In the illustrated embodiment, each ridge 280 extends substantially linearly across the circumferential axis 276 and spans a portion of the width dimension 278 of the anvil face 226. In addition, the ridges 280 are discontinuous such that gaps 279 are defined between adjacent ridges 280. The gaps 279 extend substantially linearly across the circumferential axis 276 between adjacent ridges 280 and span a portion of the width dimension 278 of the anvil face 226. Accordingly, the gaps 279 reduce the amount of surface area of the anvil face 226 that receives forces from the horn 208 (shown in FIGS. 2-7). As a result, during operation of the apparatus 200, the force required to form bonds in the nonwoven fabric is reduced. In addition, the elastic strands 120, 124, 128, 132 (shown in FIG. 1) may move more independently relative to each other than if the strands were uniformly attached in the width dimension 278.

Each ridge 280 has an extension axis 282 oriented oblique to the circumferential axis 276. In addition, the ridges 280 are positioned such that each ridge 280 overlaps adjacent ridges 280 along the circumferential axis 276. Accordingly, the ridges 280 are configured to provide continuous running contact between the horn 208 (shown in FIGS. 2-7) and the anvil 220 (shown in FIGS. 2-7) during operation of the apparatus 200 (shown in FIGS. 2-7). Moreover, the oblique extension axes 282 allow for increased spacing between the ridges 280. Also, the portion of anvil 220 that receives forces from the horn 208 may be decreased because the ridges 280 provide continuous running contact without requiring additional contact points.

In addition, in the illustrated embodiment, the ridges 280 are aligned and an alternating pattern of ridges 280 and gaps 279 extends along each extension axis 282. In alternative embodiments, the ridges 280 are arranged in any pattern that enables the anvil face 226 to function as described herein. For example, in some embodiments, at least some adjacent ridges 280 may be positioned at angles relative to each other.

In some embodiments, each ridge 280 may extend along the respective extension axis 282 a distance in a range of about 1.5 mm to about 10 mm. The gaps 279 may extend along the respective extension axis 282 a distance in range of about 0.5 mm to about 20 mm. In alternative embodiments, the ridges 280 and the gaps 279 may extend any distance that enables the anvil face 226 to function as described herein.

Figure 17:
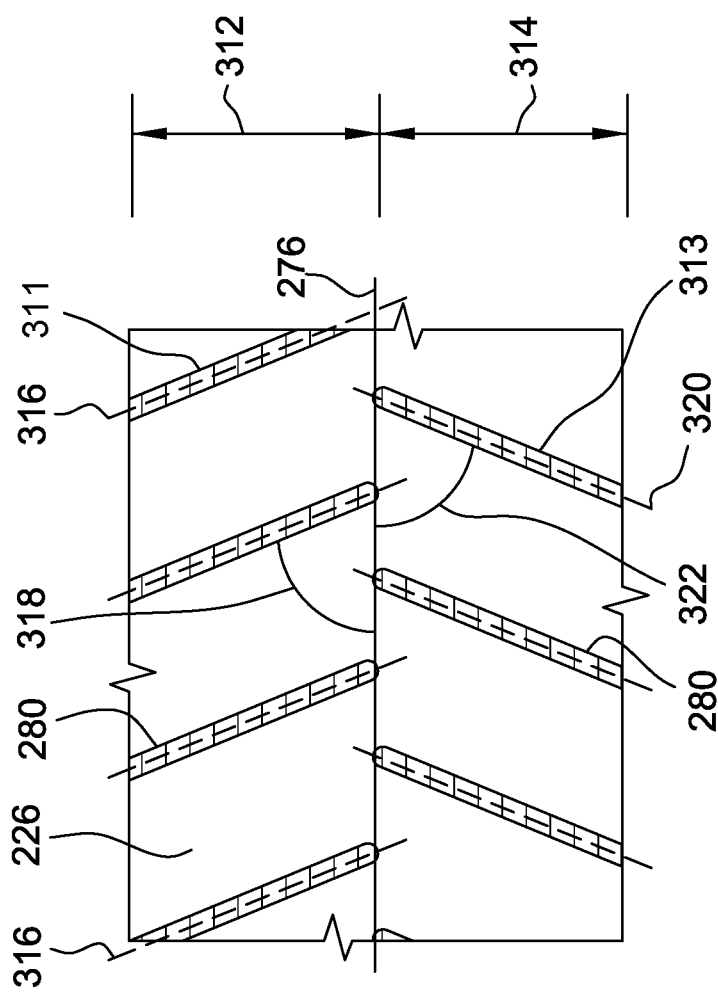
FIG. 17 is a laid-flat illustration of a portion of an annular face of yet another embodiment of an anvil for use in the apparatuses of FIGS. 2-7, the annular face including ridges extending along oblique axes.

FIG. 17 is a laid-flat illustration of another embodiment of the anvil face 226 of the apparatus 200 (shown in FIGS. 1-7). The anvil face 226 includes first ridges 311 in a first region 312 and second ridges 313 in a second region 314. In the first region 312, each ridge 311 extends along an extension axis 316. Each extension axis 316 is oriented oblique to the circumferential axis 276 such that the extension axis and the circumferential axis 276 define an angle 318. In the second region 314, each ridge 313 extends along an extension axis 320. Each extension axis 320 is oriented oblique to the circumferential axis 276 such that the circumferential axis 276 and extension axis define an angle 322. The extension axes 320 are oriented oblique to the extension axes 316. In addition, the ridges 311 in the first region 312 are offset from the ridges 313 in the second region 314. As a result, the spacing between the ridges 311, 313 may be increased and the ridges 311, 313 may be configured for continuous running contact.

Figure 18:
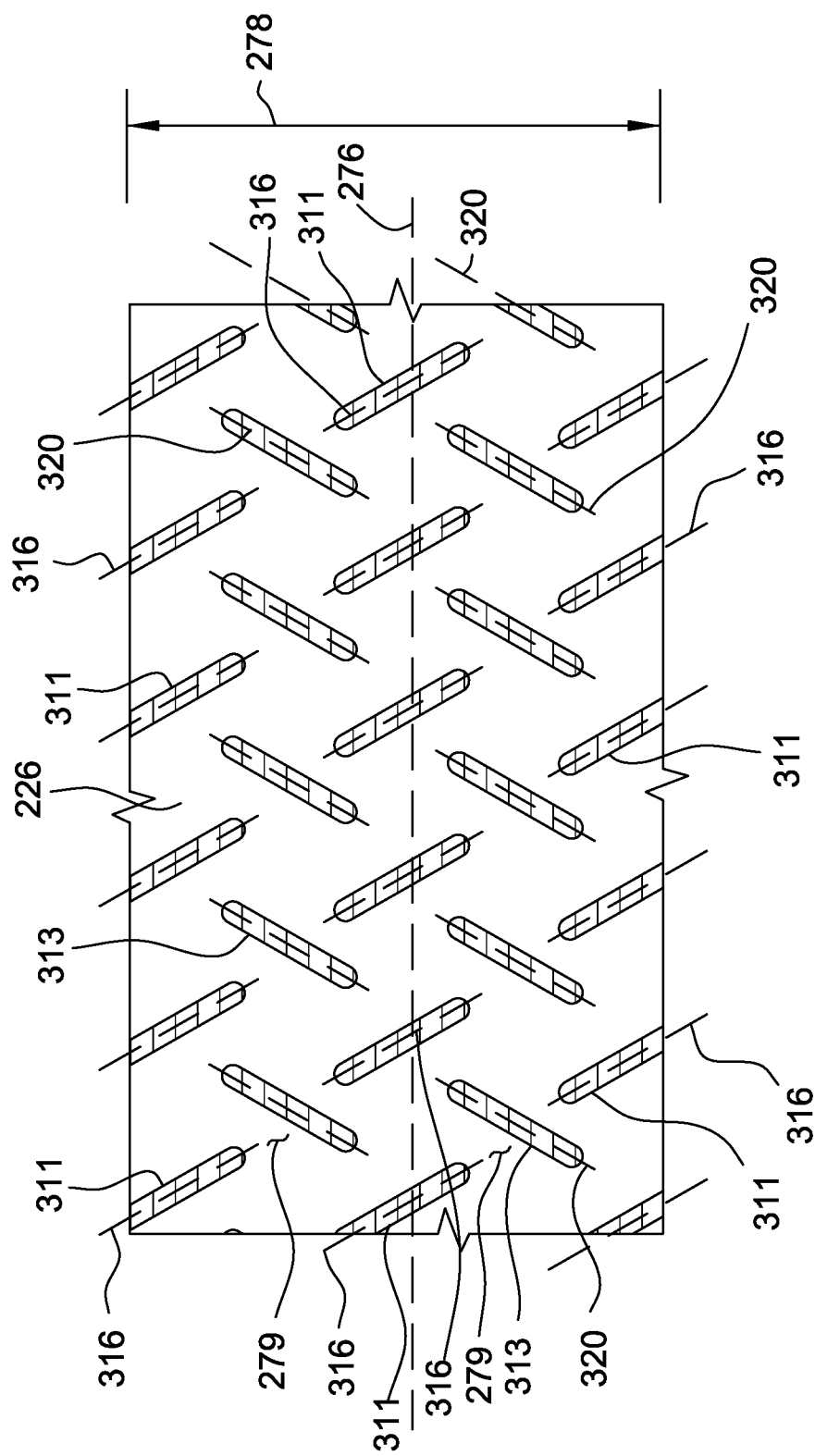
FIG. 18 is a laid-flat illustration of a portion of an annular face of yet another embodiment of an anvil for use in the apparatuses of FIGS. 2-7, the annular face including a plurality of discrete ridges.

FIG. 18 is a laid-flat illustration of yet another embodiment of the anvil face 226 of the apparatus 200 (shown in FIGS. 1-7). The anvil face 226 includes first ridges 311 and second ridges 313. In the illustrated embodiment, each first ridge 311 has an extension axis 316 oriented oblique to the circumferential axis 276 and the width dimension 278. In addition, each first ridge 311 is spaced from adjacent first ridges in the width dimension 278 and along the circumferential axis 276. Each second ridge 313 has an extension axis 320 oriented oblique to the circumferential axis 276 and the width dimension 278. Also, each second ridge 313 is spaced from adjacent second ridges in the width dimension 278 and along the circumferential axis 276. Moreover, the first extension axes 316 are oriented oblique to the second extension axes 320. In alternative embodiments, the anvil face 226 may include any ridges 311, 313 that enable the anvil face to function as described herein.

The first ridges 311 and the second ridges 313 are intermixed throughout the anvil face 226. For example, the second ridges 313 extend through the gaps 279 defined between the first ridges 311. Also, the first ridges 311 extend through the gaps 279 defined between the second ridges 313. Accordingly, each first ridge 311 overlaps adjacent second ridges 313 along the circumferential axis 276 and the width dimension 278. Each second ridge 313 overlaps adjacent first ridges 311 along the circumferential axis 276 and the width dimension 278.

The ridges 311, 313 define a pattern on the anvil face 226. In some embodiments, the pattern of ridges 311, 313 is configured to provide desired characteristics of the nonwoven elastic material. For example, the pattern of overlapping ridges 311, 313 may be configured to provide ruffling having desired characteristics (size, spacing, tension, etc.). As a result, the ruffling may provide (1) aesthetic qualities (e.g., appearance, softness), and/or (2) functional properties (e.g., for a waistband, panel, leg cuff, etc.) in one or more zones of the elastic nonwoven material. In alternative embodiments, the first ridges 311 and the second ridges 313 may be positioned in any pattern that enables the anvil face 226 to function as described herein.

Also, in some embodiments, the first ridges 311 and/or the second ridges 313 may include at least one shape of the following shapes: circular, polygonal, rectangular, sinusoidal, and ovular. In further embodiments, the first ridges 311 and/or the second ridges 313 may be configured to define an image and/or alpha-numeric character in the elastic nonwoven material. In such embodiments, some of the first ridges 311 and/or the second ridges 313 may have a substantially continuous surface to facilitate forming the desired appearance of the elastic nonwoven material.

Figure 19:
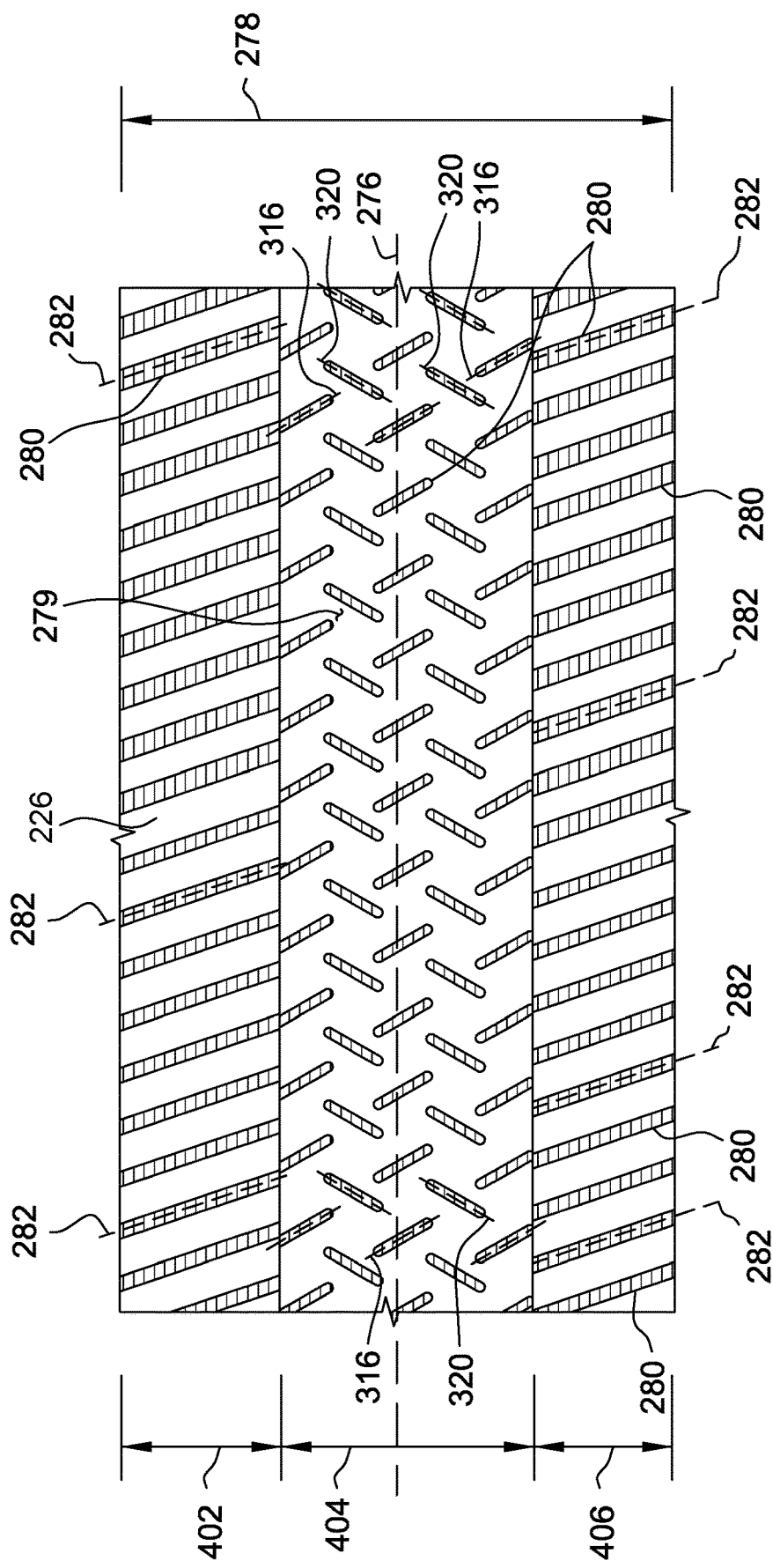
FIG. 19 is a laid-flat illustration of a portion of an annular face of yet another embodiment of an anvil for use in the apparatuses of FIGS. 2-7, the annular face including different patterns of ridges.

FIG. 19 is a laid-flat illustration of another embodiment of the anvil face 226 of the apparatus 200 (shown in FIGS. 1-7) including ridges 280 arranged in patterns. As shown in FIG. 19, the anvil face 226 includes a first region 402, a second region 404, and a third region 406. In the first region 402 and the third region 406, the ridges 280 are arranged in a first pattern in which each ridge 280 has an extension axis 282 oriented oblique to the circumferential axis 276 and the width dimension 278. In the second region 404, the ridges 280 are arranged in a second pattern in which each ridge 280 has an extension axis 316, 320 oriented oblique to the circumferential axis 276 and the width dimension 278. The extension axes 316 are oriented oblique to the extension axis 320. In addition, in the second region 404, the ridges 280 define gaps 279 therebetween and are intermixed such that adjacent ridges overlap along the circumferential axis 276 and in the width dimension. Accordingly, the first pattern and the second pattern increase the portion of the anvil face 226 that is utilized during operation of the apparatus 200.

Figure 20:
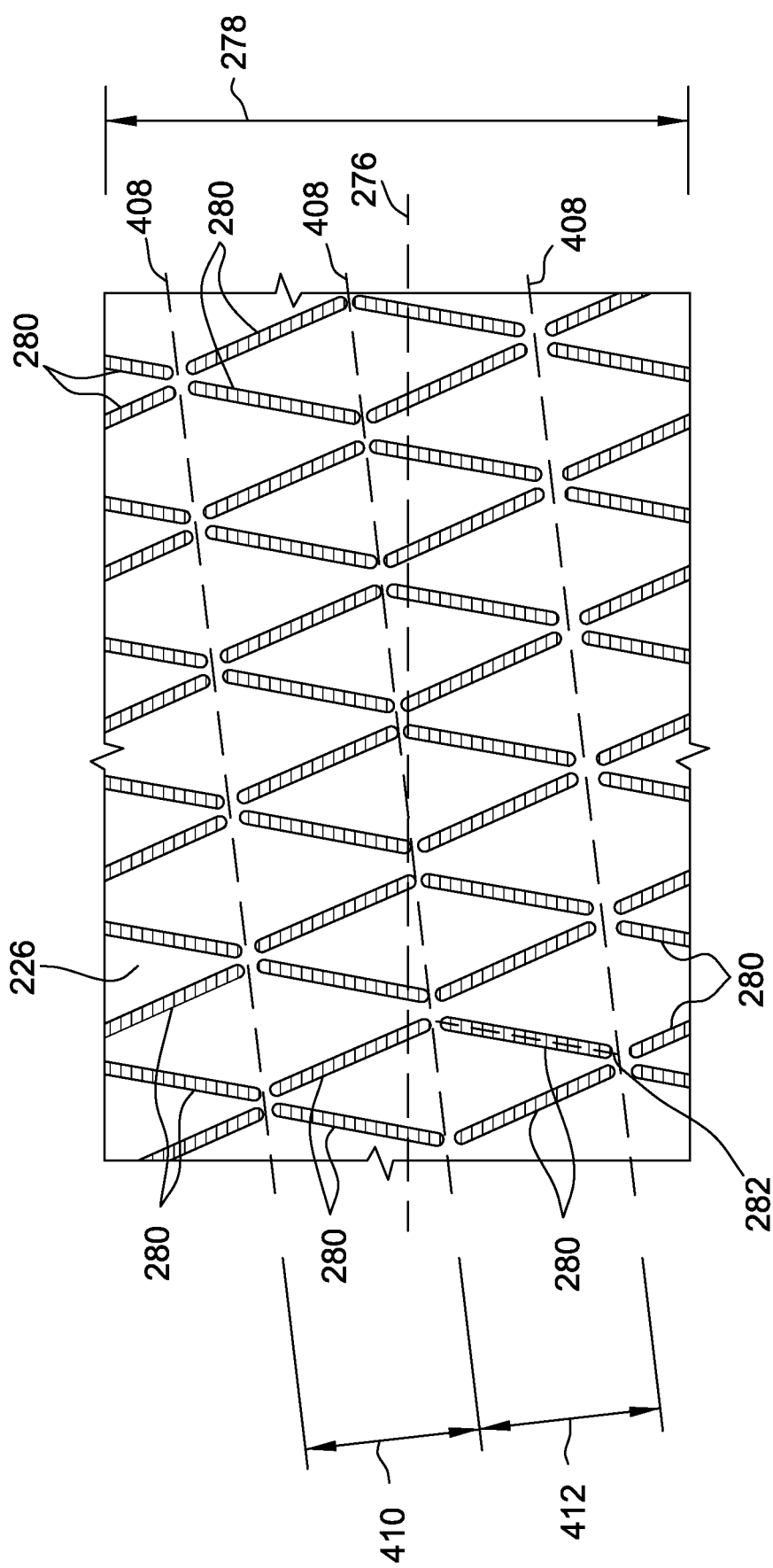
FIG. 20 is a laid-flat illustration of a portion of an annular face of yet another embodiment of an anvil for use in the apparatuses of FIGS. 2-7, the annular face including symmetric patterns of ridges.

FIG. 20 is a laid-flat illustration of another embodiment of the anvil face 226 of the apparatus 200 (shown in FIGS. 1-7) including a symmetric pattern of ridges 280. The anvil face 226 includes a first region 410 including ridges 280 and a second region 412 including ridges 280. In the first region 410, each ridge 280 has an extension axis 282 oriented oblique to the circumferential axis 276 and the width dimension 278. In the second region 412, each ridge 280 has an extension axis 282 oriented oblique to the circumferential axis 276 and the width dimension 278. An axis of symmetry 408 extends between the first region 410 and the second region 412. The ridges 280 in the first region 410 are symmetric to the ridges 280 in the second region 412 about the axis of symmetry 408. Moreover, the anvil face 226 includes a plurality of axes of symmetry 408 such that the ridges 280 form a repeating, symmetric pattern. In the illustrated embodiment, each axis of symmetry 408 is oblique to the circumferential axis 276. In alternative embodiments, the anvil face 226 may have any axis of symmetry 408 that enables the anvil face to function as described herein.

Figure 21:
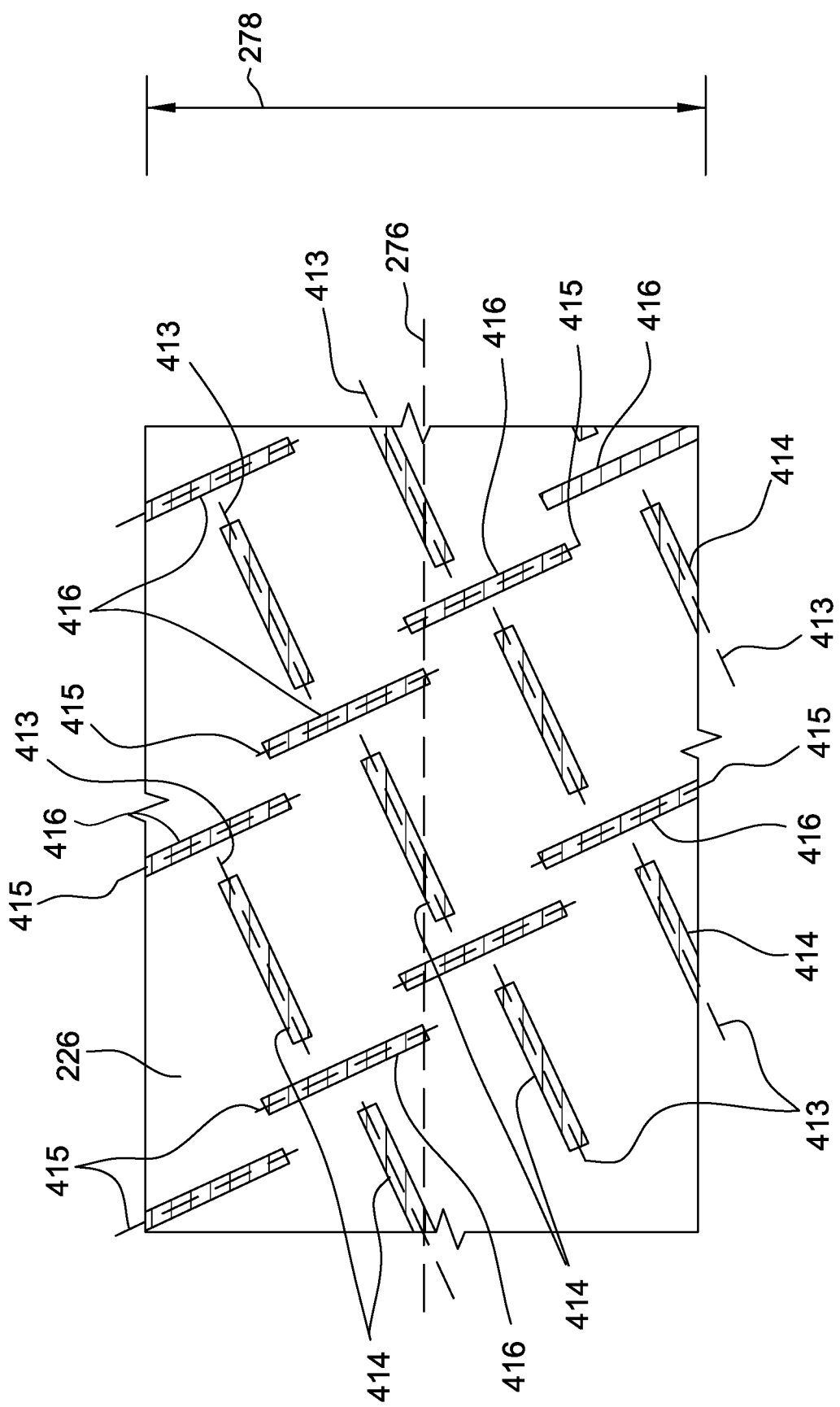
FIG. 21 is a laid-flat illustration of a portion of an annular face of yet another embodiment of an anvil for use in the apparatuses of FIGS. 2-7, the annular face including ridges that are oriented at substantially perpendicular angles to each other.

FIG. 21 is a laid-flat illustration of another embodiment of the anvil face 226 including ridges 414, 416 that are oriented at substantially perpendicular angles. The anvil face 226 includes first ridges 414 and second ridges 416. The first ridges 414 have extension axes 413 oriented oblique to the circumferential axis 276 and the width dimension 278. The second ridges 416 have extension axes 415 oriented oblique to the circumferential axis 276 and the width dimension 278. The extension axes 413 of the first ridges 414 are perpendicular to the extension axes 415 of the second ridges 416. Accordingly, the first ridges 414 and the second ridges 416 form patterns that (1) provide continuous running contact, (2) reduce the contact area of the horn 208 and the anvil 220, and (3) distribute loads throughout the anvil 220.

Figure 22:
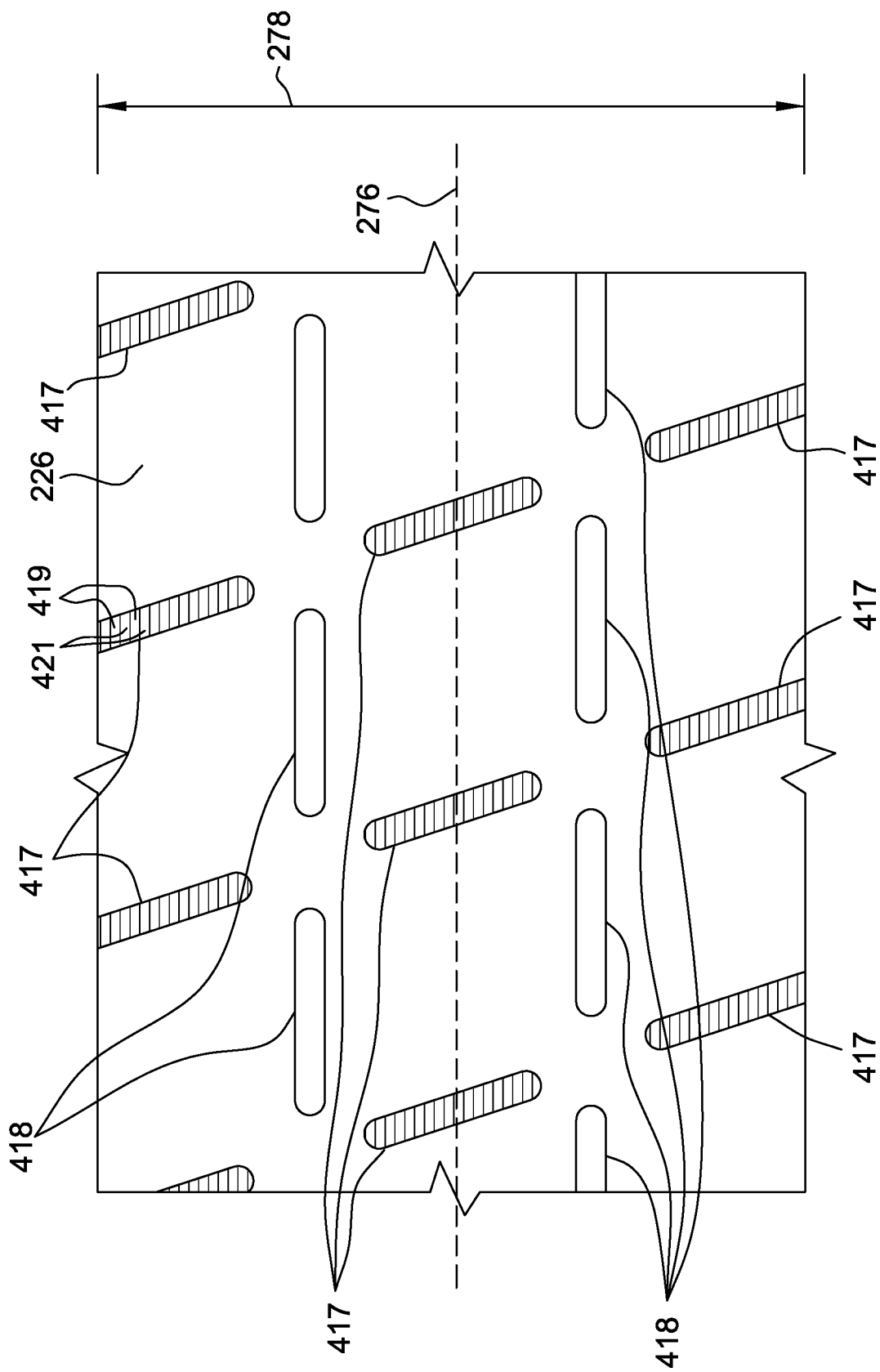
FIG. 22 is a laid-flat illustration of a portion of an annular face of yet another embodiment of an anvil for use in the apparatuses of FIGS. 2-7, the annular face including ridges.

FIG. 22 is a laid-flat illustration of another embodiment of the anvil face 226 of the apparatus 200 including first ridges 417 and second ridges 418. Each first ridge 417 may include a plurality of lands 419 and notches 421. Each second ridge 418 has a substantially continuous contour and provides a bond point in the nonwoven fabric. The first ridges 417 and the second ridges 418 are intermixed throughout the anvil face 226. Specifically, each first ridge 417 extends between adjacent second ridges 418 and each second ridge 418 extends between adjacent first ridges 417. The second ridges 418 allow for increased spacing between the first ridges 417 and provide increased bonding in the elastic nonwoven material and/or continuous running contact.

The first ridges 417 and the second ridges 418 may have any suitable shapes. For example, the first ridges 417 and/or the second ridges 418 may include orthogonal lines, dots, ovals, polygons, polygonal lines, sinusoidal lines, text, and/or any other suitable shape. In the illustrated embodiment, the first ridges 417 and the second ridges 418 are rectangular.

In addition, the first ridges 417 extend oblique to the circumferential axis 276 and the width dimension 278. The second ridges 418 extend parallel to the circumferential axis 276. Accordingly, the first ridges 417 are oblique to the second ridges 418. In alternative embodiments, the first ridges 417 and the second ridges 418 may extend in any direction that enables the apparatus 200 to operate as described herein. For example, in some embodiments, at least some of the second ridges 418 may extend oblique to the circumferential axis 276 and/or the width dimension 278.

Figure 23:
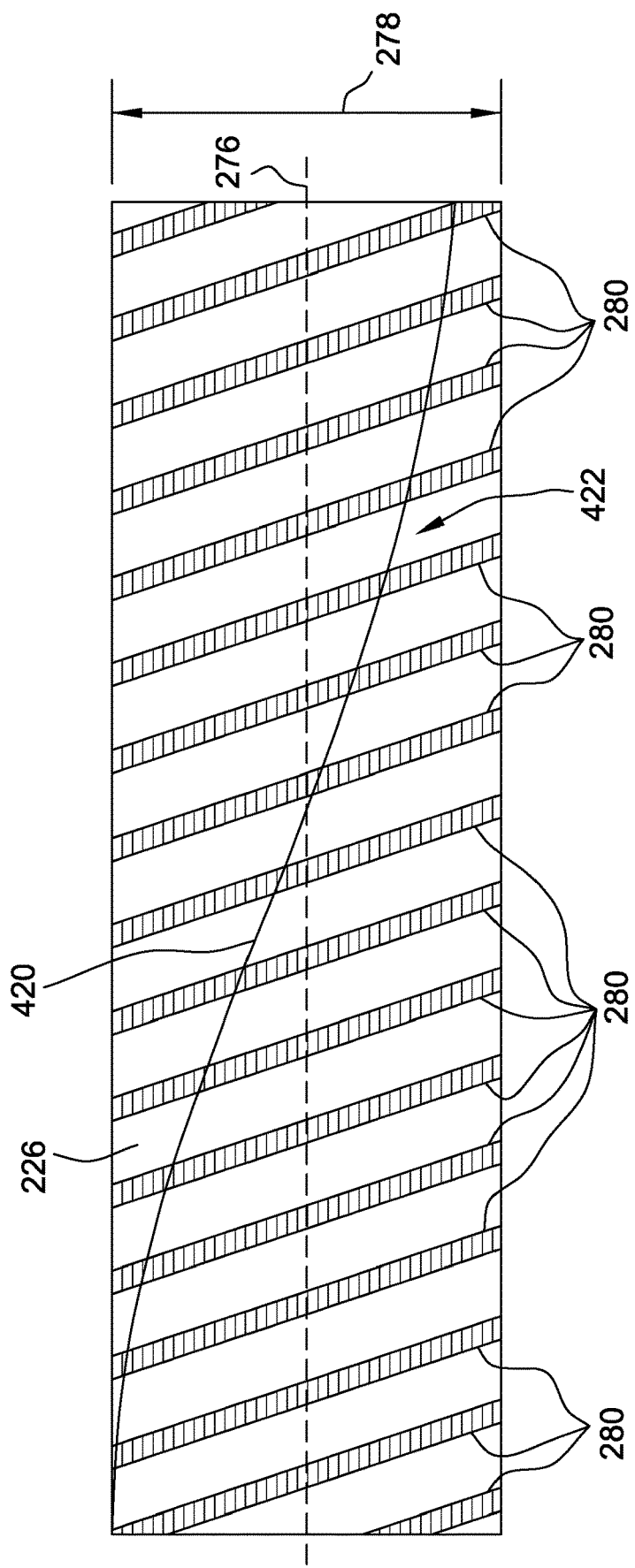
FIG. 23 is a laid-flat illustration of a portion of an annular face of yet another embodiment of an anvil for use in the apparatuses of FIGS. 2-7, and an elastic strand extending across the width of the anvil face along a curve.

FIG. 23 is a laid-flat illustration of another embodiment of the anvil face 226 of the apparatus 200. An elastic strand 420 extends across the width dimension 278 of the anvil face 226 along a curve 422 relative to the circumferential axis 276. The elastic strand 420 may be directed along the curve 422 by the supply station 102 (shown in FIG. 1). For example, with reference to FIGS. 1, 2, and 23, the supply station 102 may be configured to reciprocate and dispense the elastic strand 420 as the anvil 220 rotates such that the elastic strand 420 is received by ridges 280 on the anvil face. Due to the reciprocating motion, the elastic strand 420 may be received by varying portions of the ridges 280 such that the elastic strand 420 is directed along the curve 422. In alternative embodiments, the elastic strand 420 may be directed in any manner that enables the elastic nonwoven material to function as described herein.

Figure 24:
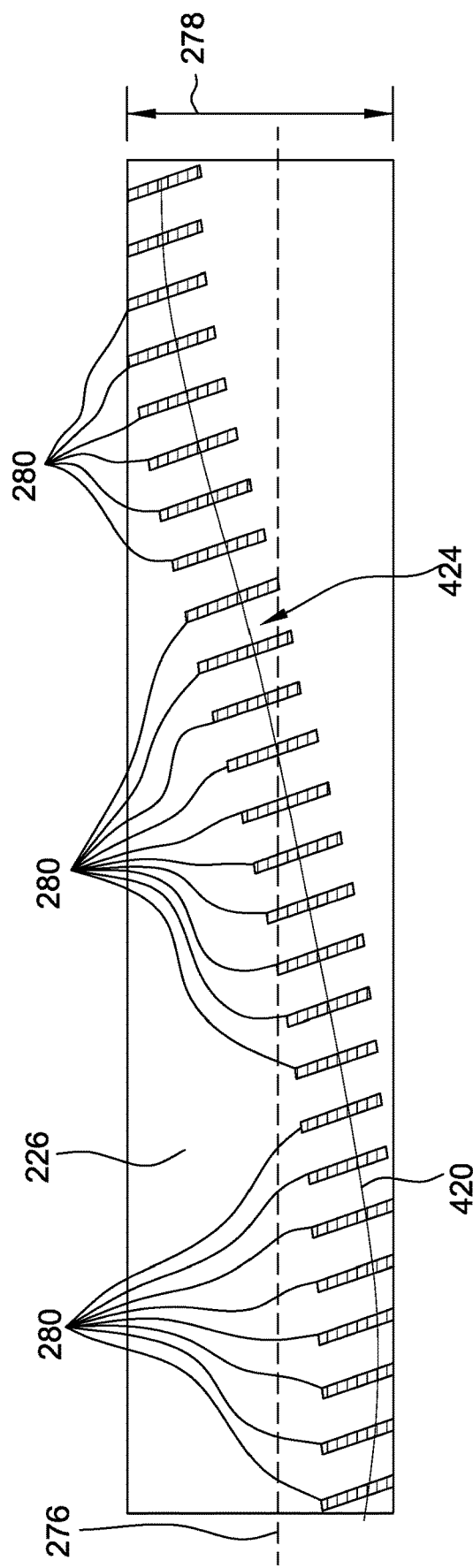
FIG. 24 is a laid-flat illustration of a portion of an annular face of yet another embodiment of an anvil for use in the apparatuses of FIGS. 2-7, and an elastic strand received and directed along a curve by ridges of the annular face.

FIG. 24 is a laid-flat illustration of another embodiment of the anvil face 226 of the apparatus 200. The anvil face 226 includes ridges 280 that extend across a portion of the width dimension 278 of the anvil face 226. The position of the ridges 280 corresponds to a curve 424 relative to the circumferential axis 276. The ridges 280 are configured to direct an elastic strand 420 along the curve 424 across the width of the anvil face 226 as the anvil 220 (shown in FIG. 2) rotates. In alternative embodiments, the elastic strand 420 may be directed in any manner that enables the elastic nonwoven material to function as described herein.

In some embodiments, the elastic strand 420 may be at least partially directed by the supply station 102 (shown in FIG. 1). For example, the ridges 280 may be configured to receive the elastic strand 420 and direct the elastic strand along a curve 424 corresponding to the reciprocating motion. In other embodiments, the supply station 102 may dispense the elastic strand 420 from a stationary position and the elastic strand may be directed along the curve 424 by any suitable means.

The elastic strand 420 may be directed along the curve 424 during a continuous entrapment process and/or an intermittent entrapment process. In addition, the elastic strand 420 may be directed along the curve 424 in a portion of the elastic nonwoven material and not necessarily throughout the entirety of the material.

Figure 25:
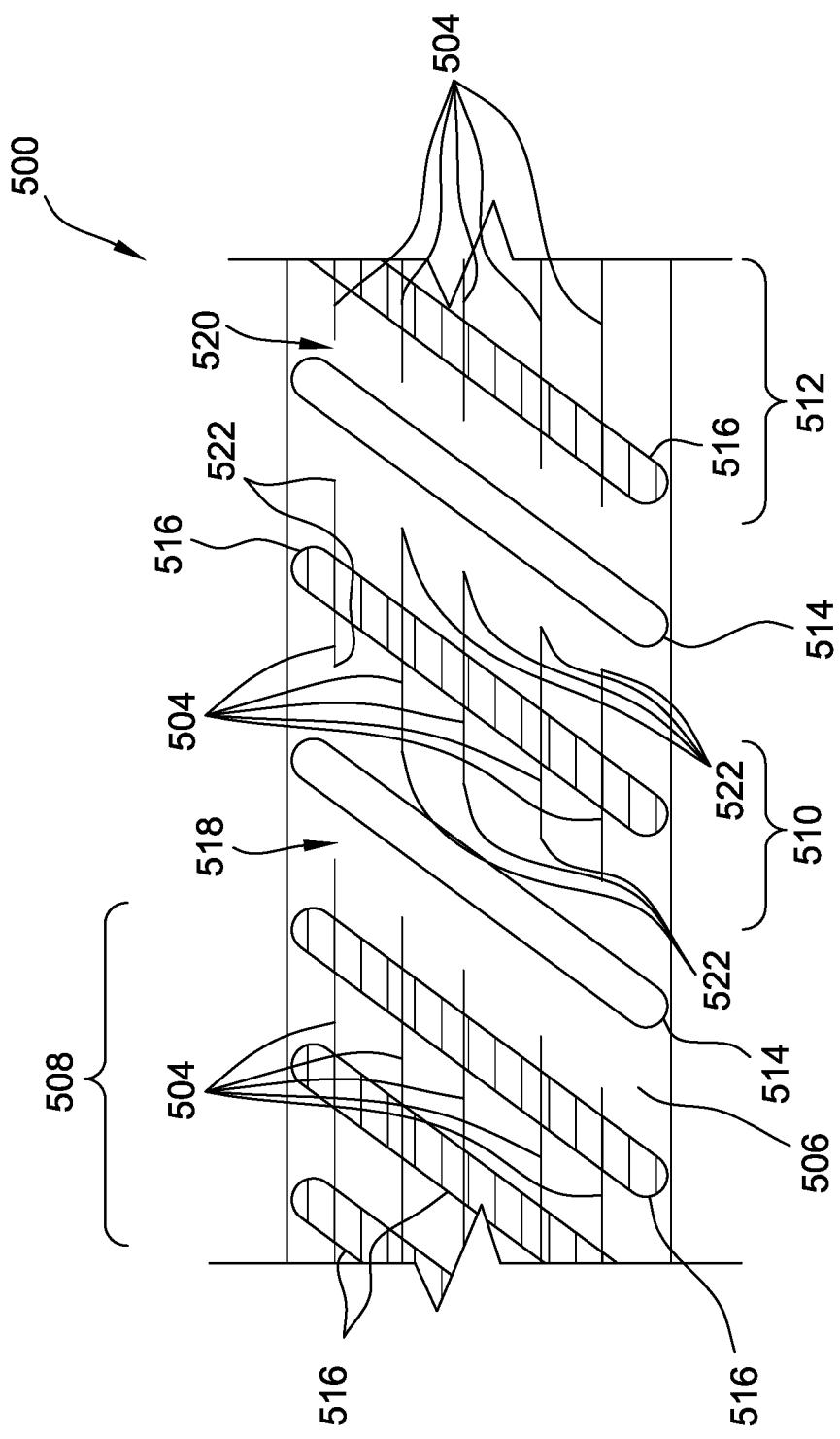
FIG. 25 is a schematic illustration of an elastic nonwoven material fabricated using an embodiment of the system of FIG. 1 and an intermittent entrapment process.

FIG. 25 is a schematic illustration of an elastic nonwoven material 500 fabricated using the system 100 and an intermittent elastic entrapment process. The elastic nonwoven material 500 includes at least one elastic strand 504 and a nonwoven fabric 506. The elastic nonwoven material 500 further includes a first region 508, a second region 510, and a third region 512. The elastic strand 504 is retained on the nonwoven fabric 506 in at least the first region 508 and the third region 512. For example, the elastic strand 504 may be entrapped within the nonwoven fabric 506 using the systems and methods described herein.

In the illustrated embodiment, the elastic strands 504 may be severed or cut by a cutting apparatus 514 between the first region 508 and the second region 510 and between the second region 510 and the third region 512. As a result, the elastic strands 504 are at least partially free in the second region 510. In some embodiments, the elastic strands 504 may be cut along a line substantially perpendicular to a longitudinal direction of the elastic nonwoven material 500. In other embodiments, the elastic strands 504 may be cut along a line extending at least partially at an oblique angle and/or parallel to the longitudinal direction. In further embodiments, the elastic strands 504 may be cut along a curve. In alternative embodiments, the elastic strands 504 may be severed in any manner that enables the elastic nonwoven material 500 to function as described herein.

The elastic nonwoven material 500 may have different elastic properties and appearances in the regions 508, 510, 512. For example, in the first region 508 and the third region 512, the elastic strands 504 are under tension and may cause the nonwoven fabric 506 to gather. In the second region 510, the elastic strands 504 are relaxed and the nonwoven fabric 506 is not caused to gather by the elastic strands.

The nonwoven fabric 506 includes at least one bond 516 in the second region 510 that is configured to retain the elastic strands 504 on the nonwoven fabric when the elastic strands are severed by the cutting apparatus 514. Specifically, the nonwoven fabric 506 is bonded between a first cut 518 and a second cut 520 such that free ends 522 of the elastic strands 504 extend on either side of the bond 516. Moreover, the bond 516 prevents free elastic strands 504 from being disbursed as debris and causing damage to or cluttering the elastic nonwoven material 500 and the apparatus 200 (shown in FIG. 1). As a result, the bond 516 reduces the cost to assemble the elastic nonwoven material 500.

The rotary ultrasonic bonding systems and methods set forth herein are utilized to directly entrap tensioned elastic within a nonwoven fabric without the use of adhesives, thereby providing various functional and commercial advantages. The systems and methods eliminate the complex adhesive delivery systems and costly adhesive materials associated with adhesive bonding processes, and the systems and methods provide a simpler, cleaner, and safer (e.g., cooler in temperature) production environment, with lower power consumption and lower material costs. Also, various functional deficiencies of adhesively bonded materials are eliminated, including adhesive bleed-through, overspray, stiffening, and creep that are common in conventional adhesively bonded materials. Thus, lower-cost nonwoven/film substrates and elastic materials can be utilized.

Moreover, the systems and methods set forth herein facilitate a more continuous production sequence (i.e., increased process uptime) due, at least in part, to the lack of: adhesive-related cleaning operations; adhesive system delivery/reliability issues; heated equipment cool-down periods in advance of maintenance events; cold-start periods; and re-heat or purge-calibrate events. Additionally, a more continuous production sequence is further facilitated by the automatic threading (or self-threading) of severed elastic strands when the system is online, as well as the use of continuously-running, over-the-end elastic spools.

Additionally, the systems and methods set forth herein are usable to attach (e.g., entrapment) elastic strands while also performing other elastic processing steps such as cutting/chopping processes, seaming processes, edge trimming processes, etc. The systems and methods are further adaptable to existing capital asset bases to provide retrofit capability (with customizable configurations if desired), as well as quicker grade-change capability as the attachment zone length changes via a software interface.

The systems and methods also facilitate maximizing elastic performance. For example, the systems and methods facilitate lowering tension at elongation as compared to other attachment methods (e.g., the systems and methods can provide a nearly pure elastic response for stress vs. strain when at least some substrates are utilized). The systems and methods also facilitate minimizing creep (or loss of performance) (e.g., the systems and methods produce elastic materials that are more robust in the face of temperature, time, and end-user solvents (e.g., emollients)) due, at least in part, to the fact that the elastic strands can be entrapped in a thermoplastic substrate, as opposed to being attached to a substrate with a susceptible intermediate binder material.

The systems and methods further facilitate customized aesthetics and functional benefits. For example, gathers are produced by a bonding pattern and/or strand-feed positioning such that size, shape, and frequency are selectable. Also, zoned tension is enabled, in that tension can be controlled by an elastic segment depending upon the desired fabric configuration (e.g., depending upon the desired cross-direction orientation within fabric (among lanes) and/or longitudinal orientation within fabric (within lanes)). Curved attachment is also facilitated if desired. Furthermore, controlled slip/creep for adjustable fit is facilitated, with intermittent or continuous attachment of elastic to the substrate being selectable to enable placement/zoning of live elastic and non-elasticized segments. Also, the systems and methods allow elastic strands to be positioned adjacent more precisely than known systems. For example, the systems do not include adhesive dispensers which can limit the placement of elastic strands relative to each other and, as a result, the described systems and methods provide a greater range of positions for the elastic strands than known systems.

Also, the systems and methods allow for the bond points and attachment points of the nonwoven fabric to be positioned in a variety of locations in machine and cross-machine directions. As a result, the systems and methods provide the ability to control the nonwoven fabric collapsing in both directions due to the force from the elastic strand. In addition, the systems and methods increase control over the functional and aesthetic properties of the elastic nonwoven material. Also, embodiments provide the capability to produce functional and aesthetic geometric and/or text features in the elastic nonwoven material. Moreover, the described systems and methods may provide the ability to control the wear characteristics of bonding modules by reducing zones of uneven engagement.

In addition to the embodiments of the systems and methods set forth above, other embodiments are also contemplated. For example, non-rotary systems of attachment (e.g., stationary (or blade) ultrasonic horns, heat, pressure, etc.) are contemplated. Also, in combination with the rotary embodiments set forth above, adhesive systems may be usable in alternative embodiments. Moreover, latent elastics may be usable instead of tensioned elastics in some embodiments. Then too, the systems and methods facilitate curving (or shifting) elastic strands with less occurrence of breakage, and the systems and methods further facilitate generating a matrix of tensions (e.g., a checkerboard effect), differential ruffling, dead zones, and/or simultaneous incorporation of elastic strands of different decitex.

Notably, the systems and methods described herein facilitate fabricating a variety of elastic nonwoven materials usable in a variety of articles such as personal care articles (e.g., adult briefs, baby diapers, child/adult pull-on pants, contour fit hygiene products, etc.) or medical garments (e.g., masks, caps, gowns, footwear, etc.). Moreover, individual components (e.g., scrim/netting, diaper ears, discreet panels, etc.) of an article can be fabricated using elastic nonwoven materials fabricated via the above-described systems and methods. Other contemplated products in which the nonwoven materials can be utilized include thermal insulation or filters (e.g., associated ruffling or blousing), as well as elastic-topped garbage bags, non-adhesive bandages, hair nets, house wrap, etc.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An apparatus for fabricating an elastic nonwoven material, said apparatus comprising:
a first bonding module; and
a second bonding module positionable in close proximity to the first bonding module, wherein at least one of the first bonding module and the second bonding module has a face with a width dimension and a circumferential axis and is rotatable about a rotation axis, the face having a plurality of ridges, each of the ridges having a plurality of interspaced lands and notches, and each of the ridges having a width and a length that is longer than the width, the ridges being spaced circumferentially about the face, wherein the ridges extend across the face by less than the width dimension, are oriented obliquely relative to the circumferential axis, and are positioned such that at least two ridges overlap along the circumferential axis such that continuous running contact is provided between the at least two ridges and one of the first and second bonding modules when rotated about the rotation axis, wherein each of the lands and each of the notches are oriented parallel to the circumferential axis and obliquely relative to the ridges.

2. The apparatus of claim 1, wherein the ridges are arranged in a pattern that is symmetric about an axis of symmetry oriented obliquely relative to the circumferential axis.

3. The apparatus of claim 1, wherein the ridges are discontinuous and define at least one gap along the face in the width dimension.

4. The apparatus of claim 1, wherein at least one ridge extends along a first oblique axis and at least one other ridge extends along a second oblique axis.

5. The apparatus of claim 1, wherein the ridges are arranged to overlap along the circumferential axis and in the width dimension.

6. The apparatus of claim 1 further comprising at least one ridge having at least one shape of the following shapes: polygonal, rectangular, sinusoidal, and ovular.

7. The apparatus of claim 1, wherein at least one ridge is configured to define at least one of an image and an alpha-numeric character in the elastic nonwoven material.

8. The apparatus of claim 1, wherein the other of the first bonding module and the second bonding module has a contour that is continuous.

9. The apparatus of claim 1, wherein the ridges extend substantially linearly across the circumferential axis.

10. The apparatus of claim 1, wherein the ridges extend non-linearly across the circumferential axis.

11. A method for fabricating an elastic nonwoven material, said method comprising:
positioning a first bonding module in close proximity to a second bonding module, wherein at least one of the first bonding module and the second bonding module includes a face with a width dimension and a circumferential axis and is rotatable about a rotation axis, the face having a plurality of ridges, each of the ridges having a plurality of interspaced lands and notches, and each of the ridges having a width and a length that is longer than the width, the ridges being spaced circumferentially about the face, wherein the ridges extend across the face by less than the width dimension, are oriented obliquely relative to the circumferential axis, and are positioned such that at least two ridges overlap along the circumferential axis such that continuous running contact is provided between the at least two ridges and one of the first and second bonding modules when rotated about the rotation axis, wherein each of the lands and each of the notches are oriented parallel to the circumferential axis and obliquely relative to the ridges;
rotating at least one of the first bonding module and the second bonding module;
directing an elastic strand between the first bonding module and the second bonding module and along a curve relative to the circumferential axis;
bonding the elastic nonwoven material in a first region, wherein at least a portion of the elastic strand is entrapped in the first region; and
bonding the elastic nonwoven material in a second region, wherein at least a portion of the elastic strand is entrapped in the second region, wherein the elastic strand extends along the curve between the first region and the second region.

12. The method of claim 11, wherein directing the elastic strand along the curve comprises feeding the elastic strand from a supply station in an oscillatory manner along the width dimension of the face.

13. The method of claim 11, wherein directing the elastic strand along the curve comprises directing the elastic strand between the notches defined in the ridges of the face.

14. An apparatus for fabricating an elastic nonwoven material including at least one elastic strand, said apparatus comprising:
a first bonding module;
a second bonding module positionable in close proximity to the first bonding module, wherein at least one of the first bonding module and the second bonding module has a face with a width dimension and a circumferential axis and is rotatable about a rotation axis, the face having a plurality of first ridges oriented obliquely relative to the circumferential axis, and a plurality of second ridges oriented obliquely relative to the plurality of first ridges and to the circumferential axis, the first and second ridges being spaced circumferentially about the face, each of the first and second ridges having a plurality of interspaced lands and notches, and each of the first and second ridges having a leading edge and a trailing edge, wherein the first and second ridges are positioned such that the trailing edge of at least one first ridge overlaps with the leading edge of at least one circumferentially adjacent second ridge along the circumferential axis such that continuous running contact is provided between the ridges and one of the first and second bonding modules when rotated about the rotation axis, wherein the first bonding module and the second bonding module are positioned to receive at least one elastic strand and a nonwoven material, wherein each of the lands and each of the notches are oriented parallel to the circumferential axis and obliquely relative to the first and second ridges; and
a supply station configured to provide the at least one elastic strand, wherein the at least one elastic strand is directed across the width dimension along a curve relative to the circumferential axis as the at least one of the first bonding module and the second bonding module is rotated.

15. The apparatus of claim 14, wherein the supply station includes at least one spool containing the at least one elastic strand, wherein the supply station is configured to direct the at least one elastic strand along the curve.

16. The apparatus of claim 15, wherein the supply station is configured to oscillate the at least one elastic strand as the at least one elastic strand is unwound from the at least one spool.

17. The apparatus of claim 14, wherein the notches and lands are arranged to receive the at least one elastic strand, the notches and lands being offset to receive the at least one elastic strand along the curve.

18. An apparatus for fabricating an elastic nonwoven material including at least one elastic strand, said apparatus comprising:
   a first bonding module;
   a second bonding module positionable in close proximity to the first bonding module, wherein at least one of the first bonding module and the second bonding module has a face with a width dimension and a circumferential axis and is rotatable about a rotation axis, the face having a plurality of ridges, wherein the first bonding module and the second bonding module are positioned to receive at least one elastic strand and a nonwoven material; and
   a supply station configured to provide the at least one elastic strand, wherein the at least one elastic strand is directed across the width dimension along a curve relative to the circumferential axis as the at least one of the first bonding module and the second bonding module is rotated, wherein the ridges have notches and lands that are arranged to receive the at least one elastic strand in the notches, the notches and lands being offset to receive the at least one elastic strand along the curve, and wherein the ridges extend along a portion of the width dimension and are arranged to correspond to the curve along the circumferential axis.

* * * * *